US006355240B1

(12) United States Patent
Dierks

(10) Patent No.: US 6,355,240 B1
(45) Date of Patent: *Mar. 12, 2002

(54) ENHANCED INSECTICIDAL INSECT VIRUS THROUGH THE EXPRESSION OF HETEROLOGOUS PROTEINS WITH EARLY PROMOTERS

(75) Inventor: Peter M. Dierks, Yardley, PA (US)

(73) Assignee: BASF Aktiengellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/686,993

(22) Filed: Jul. 25, 1996

Related U.S. Application Data

(60) Provisional application No. 60/001,603, filed on Jul. 26, 1995.

(51) Int. Cl.[7] .......................... A01N 63/00; C12N 7/01; C12P 21/00

(52) U.S. Cl. .................. 424/93.2; 435/69.1; 435/235.1; 435/320.1

(58) Field of Search .......................... 435/235.1, 320.1, 435/172.3, 69.1; 424/93.2, 199.1; 47/1.01, 58

(56) References Cited

U.S. PATENT DOCUMENTS

| | | | | |
|---|---|---|---|---|
| 5,162,222 A | * | 11/1992 | Guarino et al. | 435/172.3 |
| 5,266,317 A | * | 11/1993 | Tomalski et al. | 424/93.2 |
| 5,908,785 A | | 6/1999 | Washburn et al. | |
| 5,965,123 A | * | 10/1999 | Ahmed | 424/93.2 |
| 6,130,074 A | * | 10/2000 | Brennan | 435/91.41 |

FOREIGN PATENT DOCUMENTS

| | | | |
|---|---|---|---|
| EP | 572978 | * 12/1993 | C12N/15/86 |

OTHER PUBLICATIONS

Dickson, J.A. et al. Journal of Virology, vol. 65, p. 4006–4016, 1991.*

Xia, Y. et al. Virology, vol. 196, p. 817–824, 1993.*

* cited by examiner

*Primary Examiner*—Mary E. Mosher
(74) *Attorney, Agent, or Firm*—Elaine Sale

(57) ABSTRACT

A method is described for enhancing the efficacy of recombinant insect viruses, such as baculoviruses and granulosis viruses, for use as insecticides. This invention relates to recombinant insect viruses and vectors for use therewith in which the expression of a heterologous gene or fragments thereof (preferably encoding an insect controlling substance or modifying substance, such as an insect toxin) is operably linked to an early promoter.

14 Claims, 12 Drawing Sheets

DOSE-RESPONSE OF AaIT rNPVs ON *H. VIRESCENS*

- ■ E2 WT
- ○ DA26/CUTICLE
- ● DA26/cDNA
- ◇ 6.9K/CUTICLE
- ◆ 6.9K/SEX
- △ 6.9K/ADK
- ▲ 6.9K/CHORION
- □ Ph/CUTICLE

| Test V0323LD3 Data Summary | | |
|---|---|---|
| Tray No. | Virus Treatment | RT50 hours (95%C.I.) |
| 1 | V8:DA26/ADK-AaIT 1.1 | 41.1 (39.0-43.1) |
| 2 | V8:DA26/Chorlon-AaIT 1 | 49.1 (46.5-51.9) |
| 3 | V8:DA26/Cuticle-AaIT 1.1 | 45.1 (42.4-48.1) |
| 4 | V8EGT:DA26/ADK-AaIT 1.1 | 45.6 (43.2-48.0) |
| 5 | V8EGT:DA26/Chorlon_AaIT 3 | 50.3 (47.6-53.1) |
| 6 | V8EGT:DA26/Cuticle-AaIT 1.1 | 55.6 (52.5-58.9) |
| 7 | E2:DA26/Chorlon-AaIT | 49.0 (46.5-51.6) |
| 8 | E2 wild type | 104.7 (100.3-108.6) |

FIG.3

SEQ ID NO:24 SEQ ID NO:25

CCCCCCGGATCCATGTACAAACTGA...35nt...GCTGAGGCCAAGAAGAACGGCTAC

||||||||||||||

TTCTTCTTGCCGATG...29nt...ACGGA

SEQ ID NO:26

*Anneal Common oligo with oligo specific for the ADK signal sequence*
*Fill in single stranded regions with Sequenase 2.0*

LINE 1 SEQ ID NO:27
LINE 2 SEQ ID NO:33

BamHI

CCCCCCGGAT CCATGTACAA ACTGACCGTC TTCCTGATGT TCATCGCCTT
GGGGGGCCTA GGTACATGTT TGACTGGCAG AAGGACTACA AGTAGCGGAA

CGTGATTATC GCTGAGGCCA AGAAGAACGG CTACGCAGTC GACTCATCCG
GCACTAAAAG CGACTCCGGT TCTTCTTGCC GATGCGTCAG CTGAGTAGGC

AvaI
GAAAAGCCCC CGAGTGCCT
CTTTTCGGGG GCTCACGGA

*Fragment "B2"*

*Digest with BamHI and AvaI and ligate into pBluescript SK cut with BamHI and XmaI*

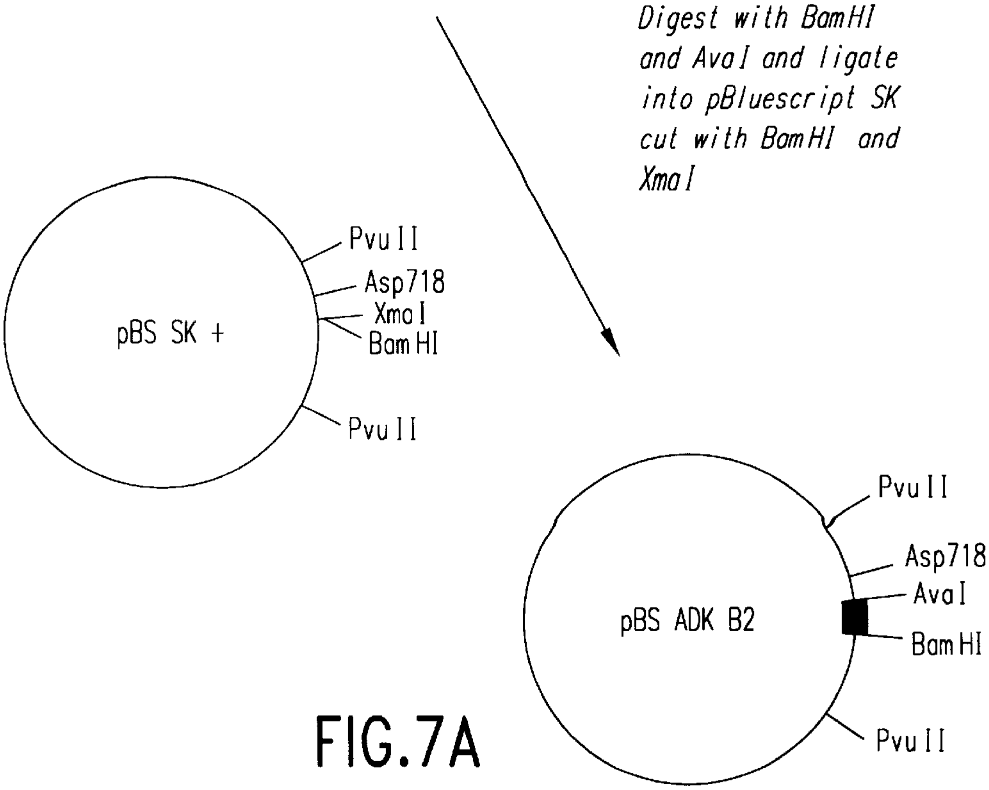

FIG.7A

SEQ ID NO:28 SEQ ID NO:29

AGCCCCCGAGTGCCTGC...65nt...CTGTCCTGCTATTGCTTC

SEQ ID NO:31

||||||||||||||

AGGACGATAACGAAG...75nt...CCTAGGCCATGGATGTC

SEQ ID NO:30

*Anneal oligos E1 and E2 for Fragment A*
*Fill in single stranded regions with Sequenase 2.0*

LINE 1 SEQ ID NO:32
LINE 2 SEQ ID NO:34

AvaI

```
AGCCCCCGAG TGCCTGCTCT CGAACTATTG CAACAATGAA TGCACCAAGG
TCGGGGGCTC ACGGACGAGA GCTTGATAAC GTTGTTACTT ACGTGGTTCC

TGCACTACGC TGACAAGGGC TACTGTTGCC TTCTGTCCTG CTATTGCTTC
ACGTGATGCG ACTGTTCCCG ATGACAACGG AAGACAGGAC GATAACGAAG

GGTCTCAACG ACGACAAGAA AGTTCTGGAA ATCTCTGATA CTCGCAAGAG
CCAGAGTTGC TGCTGTTCTT TCAAGACCTT TAGAGACTAT GAGCGTTCTC
                                 BamHI   Asp718
CTACTGTGAC ACCACCATCA TTAACTAAGG ATCCGGTACC TACAG
GATGACACTG TGGTGGTAGT AATTGATTCC TAGGCCATGG ATGTC
```

*Fragment "A"*

*Digest with AvaI and Asp718 and ligate into pBS Cuticle B7 cut with AvaI and Asp718*

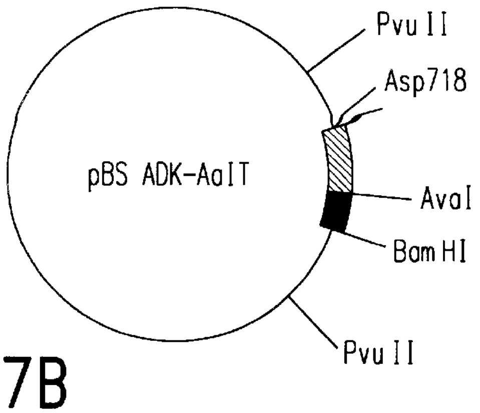

FIG.7B

SEQUENCE LISTING

```
<160> NUMBER OF SEQ ID NOS:  35

<210> SEQ ID NO 1
<211> LENGTH: 40
```

-continued

<212> TYPE: DNA
<213> ORGANISM: Artificial Sequence
<220> FEATURE:
<223> OTHER INFORMATION: Description of Artificial Sequence: cDNA

<400> SEQUENCE: 1
cctcagggca gcttaaggca gcggaccggc agcctgcagg 40

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: cDNA

<400> SEQUENCE: 2
cctgcaggct gccggtccgc tgccttaagc tgccctgagg 40

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: cDNA

<400> SEQUENCE: 3
ggatttcctt gaagagagtg ag 22

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: cDNA

<400> SEQUENCE: 4
atgaactacg tcgggctggg cctcatc 27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: cDNA

<400> SEQUENCE: 5
atgtacaaac tgaccgtctt cctgatg 27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: cDNA

<400> SEQUENCE: 6
atgttcaagt tcgtgatgat ctgcgcc 27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: cDNA

<400> SEQUENCE: 7

-continued atggccgcta aattcgtcgt ggttctg 27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: cDNA

<400> SEQUENCE: 8
atgaaactcc tggtcgtgtt cgccatg 27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: cDNA

<400> SEQUENCE: 9
atgcgcgtcc tggtgctgtt ggcctgc 27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: cDNA

<400> SEQUENCE: 10
atgttcacct tcgctattct gctcttg 27

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: cDNA

<400> SEQUENCE: 11
atgaaatttc tcctattgtt tctcg 25

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: cDNA

<400> SEQUENCE: 12
ccatgattac gccaagcgcg 20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: cDNA

<400> SEQUENCE: 13
cctcagggca gctgcctgca gg 22

<210> SEQ ID NO 14
<211> LENGTH: 30
<212> TYPE: DNA
<213> ORGANISM: Artificial Sequence -continued
<220> FEATURE:
<223> OTHER INFORMATION: Description of Artificial Sequence: cDNA

<400> SEQUENCE: 14
gctctgacgc atttctacaa ccacgactcc 30

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: cDNA

<400> SEQUENCE: 15
taatcctgca ggcagctgcc ctgaggatca gcaactatat attaagccg 49

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence: cDNA

<400> SEQUENCE: 16
gctgcctgca ggattatgta aataattaaa atgataacca tctcgc 46

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: cDNA

<400> SEQUENCE: 17
ggatttcctt gaagagagtg ag 22

<210> SEQ ID NO 18
<211> LENGTH: 100
<212> TYPE: DNA
<213> ORGANISM: Artificial Sequence
<220> FEATURE:
<223> OTHER INFORMATION: Description of Artificial Sequence: cDNA

<400> SEQUENCE: 18
agcccccgag tgcctgctct cgaactattg caacaatgaa tgcaccaagg tgcactacgc 60
tgacaagggc tactgttgcc ttctgtcctg ctattgcttc 100

<210> SEQ ID NO 19
<211> LENGTH: 110
<212> TYPE: DNA
<213> ORGANISM: Artificial Sequence
<220> FEATURE:
<223> OTHER INFORMATION: Description of Artificial Sequence: cDNA

<400> SEQUENCE: 19
ctgtaggtac cggatcctta gttaatgatg gtggtgtcac agtagctctt gcgagtatca 60
gagatttcca gaactttctt gtcgtcgttg agaccgaagc aatagcagga 110

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: cDNA -continued

<400> SEQUENCE: 20
aggcactcgg gggcttttcc ggatgaggtc gactgcgtag ccgttcttct t 51

<210> SEQ ID NO 21
<211> LENGTH: 83
<212> TYPE: DNA
<213> ORGANISM: Artificial Sequence
<220> FEATURE:
<223> OTHER INFORMATION: Description of Artificial Sequence: cDNA

<400> SEQUENCE: 21
ccccccggat ccatgtacaa actgaccgtc ttcctgatgt tcatcgcctc gtgattatcg 60
ctgaggccaa gaagaacggc tac 83

<210> SEQ ID NO 22
<211> LENGTH: 75
<212> TYPE: DNA
<213> ORGANISM: Artificial Sequence
<220> FEATURE:
<223> OTHER INFORMATION: Description of Artificial Sequence: cDNA

<400> SEQUENCE: 22
ccccccggat ccatgttcaa gttcgtgatg atctgcgccg tcctcggcct ggctgtggcc 60
aagaagaacg gctac 75

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: cDNA

<400> SEQUENCE: 23
atgtacaaac tgaccgtctt cctgatg 27

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: cDNA

<400> SEQUENCE: 24
ccccccggat ccatgtacaa actga 25

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: cDNA

<400> SEQUENCE: 25
gctgaggcca agaagaacgg ctac 24

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: cDNA

<400> SEQUENCE: 26
ttcttcttgc cgatg 15

-continued

<210> SEQ ID NO 27
<211> LENGTH: 119
<212> TYPE: DNA
<213> ORGANISM: Artificial Sequence
<220> FEATURE:
<223> OTHER INFORMATION: Description of Artificial Sequence: cDNA

<400> SEQUENCE: 27 cccccggat ccatgtacaa actgaccgtc ttcctgatgt tcatcgcctt cgtgattatc 60
gctgaggcca agaagaacgg ctacgcagtc gactcatccg gaaaagcccc cgagtgcct 119

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: cDNA

<400> SEQUENCE: 28
agcccccgag tgcctgc 17

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: cDNA

<400> SEQUENCE: 29
ctgtcctgct attgcttc 18

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: cDNA

<400> SEQUENCE: 30
aggacgataa cgaag 15

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: cDNA

<400> SEQUENCE: 31
cctaggccat ggatgtc 17

<210> SEQ ID NO 32
<211> LENGTH: 195
<212> TYPE: DNA
<213> ORGANISM: Artificial Sequence
<220> FEATURE:
<223> OTHER INFORMATION: Description of Artificial Sequence: cDNA

<400> SEQUENCE: 32
agcccccgag tgcctgctct cgaactattg caacaatgaa tgcaccaagg tgcactacgc 60
tgacaagggc tactgttgcc ttctgtcctg ctattgcttc ggtctcaacg acgacaagaa 120
agttctggaa atctctgata ctcgcaagag ctactgtgac accaccatca ttaactaagg 180

-continued

```
atccggtacc tacag                                                   195


<210> SEQ ID NO 33
<211> LENGTH: 119
<212> TYPE: DNA
<213> ORGANISM: Artificial Sequence
<220> FEATURE:
<223> OTHER INFORMATION: Description of Artificial Sequence: cDNA

<400> SEQUENCE: 33

ggggggccta ggtacatgtt tgactggcag aaggactaca agtagcggaa gcactaatag    60

cgactccggt tcttcttgcc gatgcgtcag ctgagtaggc cttttcgggg gctcacgga    119


<210> SEQ ID NO 34
<211> LENGTH: 195
<212> TYPE: DNA
<213> ORGANISM: Artificial Sequence
<220> FEATURE:
<223> OTHER INFORMATION: Description of Artificial Sequence: cDNA

<400> SEQUENCE: 34

tcgggggctc acggacgaga gcttgataac gttgttactt acgtggttcc acgtgatgcg    60

actgttcccg atgacaacgg aagacaggac gataacgaag ccagagttgc tgctgttctt   120

tcaagacctt tagagactat gagcgttctc gatgacactg tggtggtagt aattgattcc   180

taggccatgg atgtc                                                   195


<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: cDNA

<400> SEQUENCE: 35

ggagtcccgt cgacggacgt cc                                            22
```

ENHANCED INSECTICIDAL INSECT VIRUS THROUGH THE EXPRESSION OF HETEROLOGOUS PROTEINS WITH EARLY PROMOTERS

This application claims the benefit of the filing date of Provisional Application Ser. No. 60/001,603, filed Jul. 26, 1995, under 35 U.S.C. §119.

FIELD OF INVENTION

This invention relates to a method of enhancing the efficacy of recombinant insect viruses, such as baculoviruses, for use as insecticides. This invention relates to recombinant insect viruses and vectors for use therewith in which the expression of a heterologous gene or fragments thereof (preferably encoding an insect controlling substance or modifying substance, such as an insect toxin) is operably linked to an early promoter.

BACKGROUND OF THE INVENTION

The following abbreviations are used throughout this application:

AcMNPV—*Autographa californica* nuclear polyhedrosis virus bp—base pairs

BEVS—baculovirus expression vector system

ECV—extracellular virus

GV—granulosis virus kD—kilodaltons

NPV—nuclear polyhedrosis virus $occ^-$—occlusion negative virus(es)

$occ^+$—occlusion positive virus(es)

OV—occluded virus

PCR—polymerase chain reaction pfu—plaque forming unit p.i.—post-infection

PIB—polyhedron inclusion body (also known as occlusion body)

5' UTR: The mRNA or gene sequence corresponding to the region extending from the start site of gene transcription to the last base or base pair that precedes the initiation codon for protein synthesis.

3' UTR: The mRNA or gene sequence corresponding to the region extending from the first base or basepair after the termination codon for protein synthesis to the last gene-encoded base at the 3' terminus of the mRNA.

(+)strand: Refers to the DNA strand of a gene and its flanking sequences which has the same sense as the RNA that is derived from that gene.

(−)strand: Refers to the DNA strand of a gene and its flanking sequences that is complementary to the (+)strand.

Since the advent of recombinant DNA technology, there has been steady growth in the number of systems available for the regulated expression of cloned genes in prokaryotic and eukaryotic cells. One eukaryotic system that has gained particularly widespread use is the baculovirus expression vector system, or BEVS, developed by Smith and Summers (1). This system utilizes a nuclear polyhedrosis virus isolated from the alfalfa looper, *Autographa californica*, as a vector for the introduction and high level expression of foreign genes in insect cells.

*Autographa californica* multicapsid nuclear polyhedrosis virus (AcMNPV) is the prototype virus for the Family Baculoviridae. These viruses have large, circular, double-stranded DNA genomes (at least 90–230 kilobases (2)). There are two Subfamilies, Nudibaculovirinae, which do not form occlusion bodies, and the Eubaculovirinae, which are characterized by their ability to form occlusion bodies in the nuclei of infected insect cells. The structural properties of the occlusion bodies are used to further classify the members of this Subfamily into two genera: the nuclear polyhedrosis viruses (NPVs) and the granulosis viruses (GVs).

As exemplified by AcMNPV, the occlusion bodies formed by NPVs are 1–3 microns in diameter and typically contain several hundred virions embedded in a para-crystalline matrix. Occlusion bodies are also referred to as either polyhedra (polyhedron is the singular term) or as polyhedron inclusion bodies (PIBs). The major viral-encoded structural protein of the occlusion bodies is polyhedrin, which has a molecular weight of 29 kilodaltons (kD) (1,3). More than a hundred such occlusions can frequently be found in the nucleus of a single infected cell. GVs are distinguished from NPVs by the fact that their occlusions are much smaller and contain only one virion, which is embedded in a matrix of the viral protein granulin. Nevertheless, the fundamental principles of GV replication are similar to those described below for AcMNPV.

Viral occlusion bodies play an essential role in the horizontal (insect to insect) transmission of Eubaculovirinae. When a larva infected with AcMNPV dies, large numbers of occlusion bodies are left in the decomposing tissues. In neutral or acidic conditions ($pH<10$), the protein matrix and outer calyx of the occlusion body protect the embedded virions against chemical degradation in the environment and provide limited protection against UV radiation. However, when the occlusion bodies are ingested by another larva, they dissolve rapidly in the larval midgut, which is strongly alkaline (pH 10.5–12), and the embedded virions are released. These virions then adsorb to and infect various types of midgut cells.

Infected midgut cells synthesize few if any new occlusion bodies. Instead, they produce a second form of the virus, known as extracellular virus (ECV). Whereas the occluded form of the virus is responsible for the horizontal transmission of the virus among larvae, the ECV is used to spread the infection from tissue to tissue internally. This is an essential aspect of normal viral pathogenesis and continues until most tissues of the larva have been infected and lysed. As the virus spreads internally, many of the infected cells, especially hemocytes and fat body cells, produce not only more ECV, but also copious amounts of occluded virus (OV) in the form of occlusion bodies. When the larva dies, the occlusion bodies are deposited in the environment and the cycle begins anew.

Although ECV and OV are genetically identical, they are biochemically distinct. Shortly after the AcMNPV infects a cell, the nucleocapsid structure (which contains the DNA genome) migrates to the nucleus of the cell, where it is uncoated. This sets in motion a regulated cascade of viral gene expression which leads to the onset of viral DNA synthesis (at about 6–12 hours post-infection (p.i.)) and the formation of many new nucleocapsids. ECV production begins at about 10–13 hours p.i. with the budding of the nucleocapsids through the cytoplasmic surface of the cell. During the budding process, the nucleocapsids acquire a lipid membrane, or envelope, which is decorated with a viral glycoprotein known as gp64. This protein is specific to the ECV form of the virus and is required for ECV infectivity. The formation of occlusion bodies begins much later (24–36 hours p.i.) and requires the concerted action of numerous specialized viral gene products, the most prominent of which is polyhedrin.

The polyhedrin gene plays a central role in the BEVS technology. Because large amounts of polyhedrin are required for occlusion body formation, the polyhedrin gene is one of the most actively transcribed genes in the viral genome during the very late phases of virus replication. Smith and Summers (1) show that expression of a heterologous gene can be achieved by substituting the coding region of the polyhedrin gene with the coding region of a heterologous gene of interest. Since polyhedrin is not required for ECV formation, the resulting virus is able to replicate normally in cultured insect cells. However, it is no longer able to produce polyhedrin for occlusion body formation and is therefore occlusion-negative ($occ^-$).

The BEVS has been used successfully to express foreign genes isolated from a wide range of prokaryotic and eukaryotic organisms and viruses. Some representative examples include the human α- and β-interferons, the Drosophila Krueppel gene product, *E. coli* β-galactosidase, various HIV structural proteins, and a *Neurospora crassa* site-specific DNA binding protein (3). In general, these genes may encode cytosolic proteins, nuclear proteins, mitochondrial proteins, secreted proteins or membrane-bound proteins. In most cases, the proteins are biologically active and undergo appropriate post-translational modification, including proteolytic processing, glycosylation, phosphorylation, myristylation and palmitylation. Hence, this system has proven to be a highly valued tool for both fundamental molecular research and for the production of proteins for commercial purposes. Using BEVS technology, recombinant viruses are produced in cultured insect cells by homologous DNA recombination between AcMNPV DNA and a plasmid-based transfer (or transplacement) vector containing the heterologous gene of interest under the control of the polyhedrin gene promoter. To facilitate homologous DNA recombination the modified polyhedrin gene of the transfer vector is flanked at each end by several kilobases (2–4 kb is typical) of native AcMNPV DNA. Many transfer vectors conforming to this general specification have been described.

In a typical experiment, purified AcMNPV DNA and transfer vector DNA are mixed together and then transfected into Sf9 insect cells. Once the DNA reaches the cell nucleus, it can be acted upon by cellular proteins involved in the transcription, replication, topological management and repair of DNA. Most of the viral DNA is used without modification as a substrate for viral replication; however, a small fraction (typically 0.1–5%) undergoes homologous recombination with the transfer vector prior to the onset of virus replication. The product of this recombination event is a virus in which the wild-type polyhedrin gene has been transplaced by the desired heterologous gene of the transfer vector. These recombinant viruses can be identified visually with low magnification light microscopy as $occ^-$ plaques in a standard viral plaque assay.

Modification of the original BEVS technology have been described which allow the construction of recombinant viruses in which the heterologous gene is linked to appropriate regulatory sequences (e.g. promoters and signal peptides, etc.) and inserted into a site which does not disrupt the polyhedrin gene. Such viruses are able to form orally infectious polyhedra, which is generally preferred at present for a commercial insecticide. One drawback of the application of a naturally-occurring insect virus, such as a baculovirus, as a pesticide is the time required for inactivation or death of an insect, particularly when compared with chemical insecticides. Typically, insect viruses such as baculoviruses can take from 4 to 5 days to 2 weeks to kill a susectible insect, during which time the insect continues to feed and damage crops. In order to increase the activity of the insect viruses, heterologous genes producing insect controlling substances, such as toxins, have been introduced into the insect virus to enhance its speed of action on target insects. Prior to the present invention, recombinant insect viruses with enhanced speed of action against target insects contained a heterologous gene under the control of a baculovirus late or very late gene promoter, such as polyhedrin gene promoter or the p10 promoter. Such promoters were selected because they are derived from genes that are abundantly transcribed during the baculovirus life cycle. The invention provided herein further increases the efficacy (speed of action) of the recombinant insect virus upon infection of an insect cell through the use of viral early promoters.

SUMMARY OF THE INVENTION

It is an object of the present invention to construct recombinant DNA insect viruses, such as baculoviruses, and vectors for insect viruses useful for expression of a heterologous gene encoding an insect controlling substance or modifying substance, in which the expression of such a gene is operably-controlled by an early promoter. It is also an object of this invention to provide a method of expressing an insect controlling or insect modifying substance in insect cells comprising infecting insect cells with a recombinant insect virus of this invention.

It is also an object of this invention to provide an expression cassette, which comprises a gene sequence comprising the heterologous gene and an early promoter, which is operably linked to said heterologous gene for expression. Once the expression cassette is operably placed in an insect virus, the heterologous gene is expressible from the recombinant insect virus upon infecting an insect cell.

DESCRIPTION OF THE DRAWINGS

FIG. 3 is a chart summarizing the $RT_{50}$ values obtained from example 3, which tests the efficacy of an early promoter with different signal peptides in several baculovirus strains.

FIGS. 4–10 relate to the examples 15–22.

FIG. 4 depicts a schematic representation of the AcMNPV genome showing the location of the egt gene.

FIG. 6 depicts a schematic view of the organization and derivation of the DNA fragments used to assemble the (unloaded) AcMNPV V8 transfer vector NF4.

FIGS. 7A and 7B depict details of the construction of the plasmid pBS ADKAaIT, which contains the heterologous adipokinetic hormone gene signal sequence and a codon optimized cDNA sequence encoding AaIT.

FIG. 8 depicts a portion of a modular expression vector with Bsu 36I and Sse 8387I sites at opposite ends of an expression cassette containing a promoter module, a polylinker module and a 3' UTR module. The polylinker module contains an Esp 3I recognition site. The region bounded by the outermost Bsu 36I and Sse 8387I sites is defined as the virus insertion module.

FIG. 9 depicts the polymerase chain reaction (PCR) strategy for the amplification of an adipokinetic hormone gene signal/codon optimized AaIT gene, which is then digested with Bam HI.

FIG. 10 depicts a schematic representation of a modular expression vector (AC0075.1) formed by inserting the adipokinetic hormone gene signal/codon optimized AaIT into pMEV1.1, which contains the AcMNPV DA26 promoter.

DETAILED DESCRIPTION OF THE INVENTION

Figure 1:
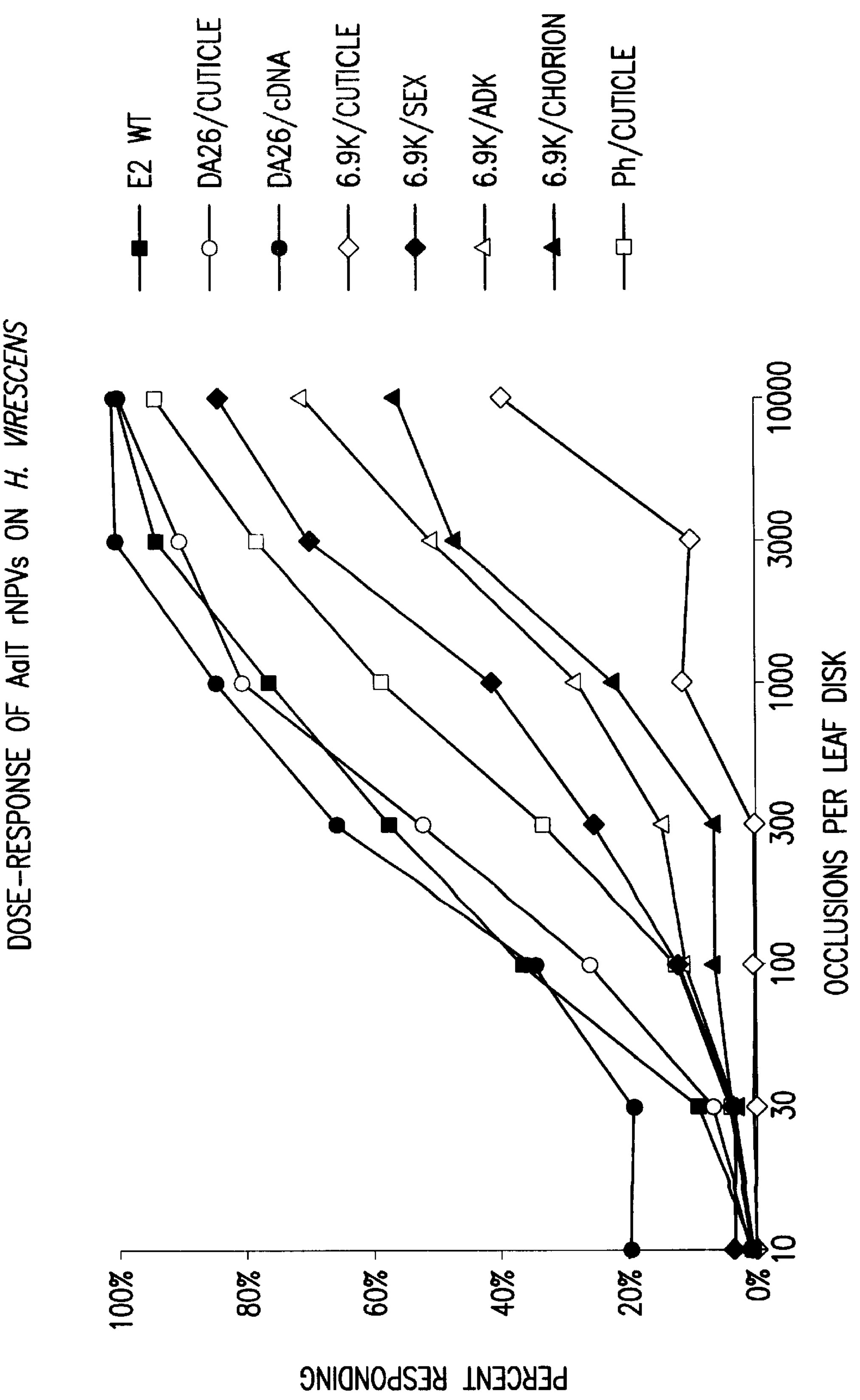
FIG. 1 depicts a dose-response graph for the insect viruses tested in example I(a).

One aspect of this invention is directed to improved recombinant insect viruses, such as baculoviruses, for use as insecticides as well as a method of enhancing the insecticidal properties of recombinant insect viruses, such as baculoviruses, for use as insecticides by inclusion of at least one heterologous gene encoding an insect controlling substance or modifying substance, such as an insect toxin, wherein the heterologous gene is present in the vector or insect virus and is operably linked to an early promoter in order that the heterologous substance is expressible from the recombinant insect virus upon introduction into an insect cell.

Applicants have discovered that for recombinant insect viruses having a heterologous gene which may encode an insect controlling substance or modifying substance, such as an insect toxin, placed under the control of an early promoter, such insect viruses have enhanced insecticidal activity over insect viruses in which the insect toxin is placed under the control of other promoters, such as a late promoter. As used in this specification, the statements "a promoter is operably linked to a gene" or "a gene is under the control of a promoter" means that the promoter controls the transcription of the gene. In general one early promoter is operatively linked to the heterologous gene; however, more than one early promoter may be used.

Promoters

Viral early promoters useful in this invention are well known in the art. The early promoters useful in this invention are derived from early viral genes, which genes are activated prior to the onset of viral DNA synthesis (i.e. replication of the viral genome). Preferably, such viral genes are early promoters which are (i) activated either almost immediately or within about 60 minutes, more preferably within about 30 minutes after the virus enters a susceptible insect cell or (ii) activated more than 60 minutes but within about 12 hours, more preferably within about 6 hours, after the virus enters a susceptible insect cell. The time for activation can vary based on the multiplicity of infection (i.e. number of infectious viral particles used per cell). For the above, the number of plaque-forming units of virus (pfu) used per cell is about 10 to 20.

In general, the early genes include those that (a) have been identified empirically as being expressed during the early phase (i.e., before DNA synthesis) of the replication cycle of an insect virus, such as a AcMNPV replication cycle or (b) are predicted to be expressed early in the insect virus life cycle (e.g. AcMNPV life cycle) based on the presence of enhancer-like elements, conserved cap sequences and/or TATA box sequences in the first 160 bp upstream of the ATG start codon of the gene, or (c) are homologs of AcMNPV early genes in other nuclear polyhedrosis viruses. A listing of the genes meeting these criteria in AcMNPV has been presented by Ayres et al. (1994), Martin D. Ayres, The complete DNA sequence of *Autographa californica* nuclear polyhderosis virus. Virology 202:586–605., which is incorporated herein by reference. Especially preferred embodiments are directed to promoters from the following known early genes: DA26 (orf 16), 35K (orf 135), ie-1 (orf 147), ie-n (orf 151), PE38 (orf 153), ME53 (orf 139) and gp67 (orf 128). The DA26 and 35K gene promoters are particularly preferred.

This invention relates to gene sequences encoding the natural viral promoters or synthetic promoters which may differ from the naturally-occurring promoter sequence or known promoter sequence by modifications to the sequence, permitting retention of substantially the same functional activity in expressing a desired heterologous gene as the activity of a recombinant insect virus employing an unaltered or modified promoter of this invention. The sequence may be modified by at least one additional deletion, insertion or substitution of nucleotides of a known promoter gene. Preferably, the modified promoter sequence is at least 60% homologous to the unmodified gene, preferably 70% and more preferably 80 to 90% homologous. The homology can be determined by comparing the number of similar nucleotides or by comparing the number of preserved critical nucleotides or preserved nucleotide regions, with the latter two methods being preferred.

Although in this invention early promoters may be used with other types of promoters, such as late promoters, preferably, the heterologous gene is operably linked to only early promoters. Operably linking a single early promoter to a heterologous gene is sufficient for the purposes of this invention although more than one early promoter may be employed.

Insect Modifying Substances and Toxins

Any heterologous gene encoding an insect controlling or insect modifying substance may be used. These substances control or modify the insect by decreasing its ability to live and or feed on plants. The action of such substances, e.g. toxins are well-known in the art. Many of these genes are well-known in the art.

Generally, a heterologous gene is selected which contains an open reading frame flanked by in-frame translation initiation and termination codons, and which may be inserted into an insect virus or vector for expression of the heterologous gene. Therefore, all the heterologous genes which have been expressed in the BEVS are also expressible in accordance with this invention.

In a particularly preferred embodiment of this invention, the nucleic acid sequence encoding a heterologous protein is selected from the group consisting of toxins, neuropeptides and hormones, and enzymes.

Such toxins include a toxin from the mite species Pyemotes tritici, the toxin AaIT from *Androctonus australis* (9), a toxin isolated from spider venom (28), a toxin from *Bacillus thuringiensis* subsp. *aizawai* (29), and a toxin from *Bacillus thuringiensis*_CryIVD. (30) Such neuropeptides and hormones include eclosion hormone, prothoracicotropic hormone, adipokinetic hormone, diuretic hormone and proctolin. An example of an enzyme is juvenile hormone esterase.

In one of the alternatively preferred embodiments, the heterologous gene encodes a relatively small insect toxin, which is about 100 or less amino acids in length. In such additional embodiments, such toxins contain an abundance of cysteine residues (herein also referred to as "cysteine-rich" toxins). Although toxins which are not cysteine-rich can benefit from the discovery of this invention, it is believed that relatively small cysteine-rich toxins are further advantaged by use with an early promoter of this invention. These cysteine-rich toxins can possess relatively high activity against insects when expressed from early promoters. Preferably, the toxins having about 40 to about 100 amino acids contain at least 6 or more cysteine residues, and for toxins having less than 40 amino acids, these toxins should preferably contain at least 4, or more cysteine residues. Such toxins would be expected to be found in a wide variety of venomous invertebrates, including scorpions, spiders, parasitic wasps, centipedes, millipedes, Cnideria (hydras, jellyfish, sea anemones and corals) and cone snails. Specific examples of such toxins include:

AaIT (North African scorpion, *Androctonus australis*) LqhIT2, LqqIT2, BjIT2, LqhP35 (Buthoid scorpions) SmpIT3, SmpCT2, SmpCT2, SmpMT (Chactoid scorpions) DK 9.2, DK 11, KD 12 (spider Deguetia) μ-agatoxins, (funnel web spider, Agelenopsis aperta) King Kong toxin (cone snail, Conus textile) Pt6 (primitive hunting spider, *Plectreurys tristis*) NPS-326, NPS-331, NPS-373 (spider, *Tegenaria agrestis*) Tx4(6-1) (armed spider, *Phoneutri nigriventer* (Keys)).

Although the invention will be exemplified for AaIT, it is understood that the concepts described herein are applicable for all the above-listed insect controlling or modifying substances, as well as for other heterologous proteins. The known native nucleotide sequence for the gene encoding AaIT may be used. However, a modified nucleotide sequence may also be used.

The degeneracy of the genetic code permits variations of the nucleotide sequence, while still producing a polypeptide having the identical amino acid sequence as the polypeptide encoded by the native DNA sequence. The procedure known as codon optimization provides one with a means of designing such an altered DNA sequence.

The design of codon optimized genes should take into account a variety of factors, including the frequency of codon usage in an organism, nearest neighbor frequencies, RNA stability, the potential for secondary structure formation, the route of synthesis and the intended future DNA manipulations of that gene. One such codon optimized AaIT nucleotide sequence is that set forth in nucleotides 49–258 of the sequence designated "SEQ ID NO:29", as disclosed in U.S. application Ser. No. 08/070,164 filed on May 28, 1993, which is published as PCT application U.S. Ser. No. 94/06079, filed May 27, 1994 (referenced in this application as N. Webb et al.), which is incorporated herein by reference. In many embodiments of this invention, the heterologous gene encodes a codon optimized gene for a toxin and for signal sequence.

Signal Peptides

In many applications, the heterologous gene inserted into the baculovirus may include a nucleotide sequence encoding a signal peptide. Signal sequences are required for a complex series of post-translational processing steps which result in secretion of a protein. If an intact signal sequence is present, the protein being expressed enters the lumen of the rough endoplasmic reticulum and is then transported through the Golgi apparatus to secretory vesicles and is finally transported out of the cell. Generally, the signal sequence immediately follows the initiation codon and encodes a signal peptide at the amino-terminal end of the protein to be secreted. In most cases, the signal sequence is cleaved off by a specific protease, called a signal peptidase. Signal sequences improve the processing and export efficiency of recombinant protein expression using viral expression vectors. Where the heterologous protein is an insect controlling protein, optimized expression of the insect controlling protein using an appropriate signal sequence achieves more rapid lethality than wild-type insect virus.

If the native AaIT gene is used, it typically will be immediately downstream of the native AaIT signal peptide, which is encoded by the nucleotide sequence designated in PCT Application U.S. Ser. No. 94/06079 as "SEQ ID NO: 28". However, it is possible to use a heterologous signal peptide, particularly a signal peptide from an insect species. Seven such insect signal peptides are as follows (listed by type, species, codon optimized and native sequences including SEQ ID NOS: designated in PCT Application U.S. Ser. No. 94/06079): the cuticle signal sequence from *Drosophila melanogaster* (SEQ ED NOS:29, nucleotides 1–48;40), the chorion signal sequence from *Bombyx mori* (SEQ ID NOS:38,39), the apolipophorin signal sequence from *Manduca sexta* (SEQ ID NOS:36,37), the sex specific signal sequence from *Bombyx mori* (SEQ ID NOS:43,44), the adipokinetic hormone signal sequence from *Manduca sexta* (SEQ ID NOS:34,35), the pBMHPC-12 signal sequence from *Bombyx mori* (SEQ ID NOS:32,33) and the esterase-6 signal sequence from *Drosophila melanogaster* (SEQ ID NOS:41,42).

Fragments derived from various modular expression vectors containing the gene for AaIT can be ligated in vitro into the direct ligation virus vectors, such as 6.2.1 and A4000 described in N. Webb et al.

Insect Virus

The insect viruses which are employed in this invention generally include double stranded enveloped DNA viruses such as (Subfamily, then species) Entomopoxvirinae (*Melolontha melolontha* entomopoxvirus), Eubaculovirinae (*Autographa californica* MNPV; *Heliocoverpa zea* NPV; *Trichoplusia ni* GV), Nudibaculovirinae (*Heliocoverpa zea* NOB), *Helicoverpa zea* GPV as well as double stranded nonenveloped DNA viruses such as the family Iridoviridae (Chilo iridescent virus). These insect viruses typically have genomes at least 90 kb in size (2).

Over 400 baculovirus isolates have been described. The Subfamily of double stranded DNA viruses Eubaculovirinae includes two genera, nuclear polyhedrosis viruses (NPVs)

and granulosis viruses (GVs), which are particularly useful for biological control because they produce occlusion bodies in their life cycle. Examples of NPVs include *Lymantria dispar* NPV (gypsy moth NPV), *Autographa californica* MNPV, *Anagrapha falcifera* NPV (celery looper NPV), *Spodoptera littoralis* NPV, *Spodoptera frugiperda* NPV, *Heliothis armigera* NPV, *M amestra brassicae* NPV, *Choristoneura fumiferana*, NPV, *Trichoplusia ni* NPV, *Heliocoverpa zea* NPV, Rachiplusia NPV, etc. Examples of GVs include *Cydia pomonella* GV (codling moth GV), *Pieris brassicae* GV, *Trichoplusia ni* GV, *Artogeria rapac* GV, *Plodia interpunctella* GV (Indian meal moth), etc. Examples of entomopoxviruses include *Melolontha melolontha*_EPV, *Amsacta moorei*_EPV, *Locusta migratoria* EPV, *Melanoplus sanguinipes* EPV, *Schistocerca gregaria* EPV, *Aedes aegypti* EPV, *Chironomus luridus* EPV, etc.

The *Autographia californica* nuclear polyhedrosis virus (AcMNPV) is the prototype virus of the Family Baculoviridae and has a wide host range. The AcMNPV virus was originally isolated from *Autographa californica*, a lepidopteran noctuid (which in its adult stage is a nocturnal moth), commonly known as the alfalfa looper. AcMNPV has an approximately 130 kb genome (6). This virus infects 12 families and more than 30 species within the order of Lepidopteran insects (7).

Although the invention will be exemplified for *Autographa californica* NPV (AcMPNV), it is understood that the concepts described herein are applicable for all the above-listed insect viruses. It is further contemplated that the present invention will be highly useful in improving new insect viruses which are not yet identified and classified in the literature.

Methods For Using Promoters

Methods for use of the early promoters in expressing heterologous proteins in insect viruses are well-known in the art. Such methods are disclosed by L. Miller et al in PCT Publication Number WO 90/14428 (published Nov. 29, 1990) on "Improved Expression Vectors", R. Possee et al. in EP Patent Application 90305025 (published Nov. 14, 190 with publication number 0 397 485), P. Christian et al in PCT Publication WO 93/03144 (published Feb. 18, 1993), and K. Iatroa in PCT Application CA93/00267 (filed Jun. 26, 1993) and are incorporated herein by reference. Additional methods of constructing expression vectors with promoters are previously described by Sambrook et al. In one preferred embodiment, the early promoters are used in modular expression vectors and direct ligation virus vectors, both of which are disclosed in U.S. application Ser. No. 08/070,164 filed on May 28, 1993, which was published as PCT application U.S. Ser. No. 94/06079, filed May 27, 1994 (referenced in this application as N. Webb et al.).

The present invention is directed, in part, to the discovery of an expression cassette which can be used to generate recombinant baculoviruses that can express heterologous proteins under the control of a viral promoter in substantially all tissues of the insect.

An expression cassette comprises an early promoter and a termination sequence. The cassette also contains a linker sequence comprising a number of unique restriction sites into which the desired structural gene encoding a heterologous protein may be inserted. The desired heterologous gene is inserted into the expression cassette such that the structural gene is operatively linked to the promoter. Another vector can also be constructed which contains a portion of the baculovirus that can sustain insertions of non-viral DNA fragments. The recombinant expression cassette containing the heterologous gene is excised from the first vector by digestion with restriction endonucleases and inserted into a nucleotide site in the baculovirus sequence present on the other vector, thereby creating a transplacement vector. The recombinant expression cassette and the transplacement vector are transfected separately into insect cells for expression of the heterologous protein. The transplacement vector is also co-transfected into insect tissue culture cells with wildtype baculovirus DNA which is homologous to the portion of baculovirus DNA present on the transplacement vector. Recombinant baculovirus genomes containing the expression cassette are generated by double cross-over events. Such recombinant viruses are used to infect insect cells for the expression of the heterologous protein.

Whether present as a gene sequence or expression cassette, an early promoter is able to direct the expression of a heterologous protein operatively linked to the promoter when the sequence or expression cassette is introduced into insect cells.

Additional embodiments are directed to insecticidal compositions which comprise the recombinant insect virus of this invention. The composition may be formulated using known methods. The composition can be formulated in the same manner as an ordinary chemical pesticide. The recombinant insect virus is combined with a suitable carrier which allows the recombinant insect virus to retain its activity upon infection of an insect cell. The insecticidal compositions may be in the form of wettable powder or sprayable liquid.

In order to compare heterologous gene expression from the early promoters to that obtained from the late promoter, a recombinant virus containing the AaIT structural gene coding sequence inserted downstream of the polyhedrin promoter was tested in the following example.

EXAMPLES

Unless otherwise noted, standard molecular biological techniques are utilized according to the protocols described in Sambrook et al. (10). Standard techniques for baculovirus growth and production are utilized according to the protocols described in Summers and Smith (6). All references to "named" AcMNPV restriction fragments are based on the physical maps of the E2 strain of AcMNPV published in Summers and Smith (6). For example, the designation Eco RI "I" refers to the fragment identified as "I" on the linear map of restriction endonuclease fragments produced by digestion of AcMNPV strain E2 DNA with Eco RI (FIG. 1).

Example 1

As noted above, the promoters are placed in modular expression vectors (MEVS) and then into a direct ligation vector 6.2.1, which are disclosed in the published N. Webb et al. PCT publication identified supra The location of insertion of the gene promoter, along with the gene for the signal peptide and selected heterologous gene, in the recombinant insect viruses and vectors used herein is as provided in the strain preparations as described herein. The insertion site is at residue −92 upstream of the start codon of the polyhedrin gene. Details regarding specific preparations of recombinant insect viruses and vectors used are provided in Examples 5–22 below. Once the recombinant insect virus is prepared with each promoter, each is tested in the following bioassay.

DNA Sequences and Constructs

All of the AaIT gene constructs used have been assembled using the MEVS design as disclosed N. Webb et al. With the exception of the AaIT gene designated as the AaIT cDNA gene (or as AaHIT1), all of the AaIT genes use the codon optimized AaIT DNA sequence described in copending U.S. application Ser. No. 08/009,264, filed Jan. 25, 1995, which is incorporated herein. Also, with the exception of the AaIT gene designated as the AaIT cDNA (or as AaHIT1), all of the signal peptides linked to the AaIT coding region have codon optimized DNA sequences as described in copending U.S. application Ser. No. 08/009,265, filed Jan. 25, 1995, which is incorporated herein. The sequence of the AaIT cDNA gene, which uses the native DNA sequence for both the signal peptide and toxin coding region, has also been disclosed in applications Ser. Nos. 08/009,264 and 08/009,265.

The DNA sequences of the promoter modules have also been disclosed in the N. Webb et al patent application as follows: DA26 in FIG. 11; 35K in FIG. 12; 6.9K in FIG. 12; polyhedrin in FIG. 14. The DNA sequences of the 3' untranslated regions (3' UTR) of each AaIT gene construct are disclosed in FIGS. 9 and 16 of the same application.

Bioassay method

A standard leaf disk assay is performed on third instar *Heliothis virescens* larvae to determine the dosage of virus required to achieve 50% mortality in the test insect population (i.e., the $LD_{50}$). A one microliter droplet containing a defined dose of PIBs in TET buffer (50 mM Tris-HC 1 (pH 7.5)/10 mMEDTA/0.1% Triton™ X-100 (Rohm and Haas, Philadelphia, Pa.) is added to a 5 mm cotton leaf disk in an individual well of a multiwell tray containing a filter paper disk (approximately 4 mm diameter) that has been pre-moistened with 30 $\mu$l of water. After the droplet dries, a single larva is placed in the well and the well is closed. The larvae are allowed to feed overnight. The next morning, larvae which have consumed the entire leaf disk are transferred to individual wells containing insect diet. The larvae are monitored for morbidity and mortality at least once per day until survivors pupate. A responding insect is one which is either dead or sufficiently moribund that it is unable to right itself within 1–2 minutes after being tipped on its back. Such moribund larvae include those exhibiting symptoms of AaIT toxicity (i.e., contractile paralysis), which is generally evident 24–36 hours before the larvae die. Insects that consume leaf disks treated with TET buffer alone are used as negative controls.

$LD_{50}$ values are determined by probit[2] analysis of the dose/mortality data. D. Finney, Probit Analysis, Cambridger Press, 1952. The median response time ($RT_{50}$) is determined by probit analysis of the time/response data at a single dose of virus (generally either $10^4$ or $10^5$ PIBs) that is sufficient to produce 95% or greater mortality in the test insect population. Only insects that respond to the treatment at the specified dose are included in the $RT_{50}$ determination.

The constructs listed below contain various promoters regulating AaIT gene expression, all linked to the cuticle signal sequence. The promoters are: 1) DA26 (early) 2) 35K (delayed early) 3) 6.9K (late) and 4) polyhedrin (very late). Two constructs contained the hr5 enhancer. In order to identify how effective these recombinants are, these constructs were tested at least in duplicate on third instar *Heliothis virescens* using the above leaf disk method and $LD_{50}$ and $RT_{50}$ values were generated.

This data is compiled over a wide range of leaf disk assays, i.e., these tests were not run side-by-side, although the values for the wild-type remained stable between tests. $LD_{50}$ and $RT_{50}$ values for three of the six constructs were generated and are listed in Table 1. In a separate set of tests, we tested the remaining three constructs at a single does of 100,000 PIBs, where $RT_{50}$ values were generated and are listed in Table 2.

DATA AND RESULTS

TABLE 1

$LD_{50}$ and $RT_{50}$ Values for Third Instar Heliothis Virescens from Leaf Disk Assays 8 Days After Treatment

| Construct Promoter/Signal | $LD_{50}$ (95% Confidence Interval) Expressed in PIBs @ 8 DAT | $RT_{50}$ (95% Confidence Interval) Expressed in Hours @ 10,000 PIBs |
|---|---|---|
| E2 Wild-type | 245 (201,299) | 105 (97,114) |
| DA26/cuticle | 283 (231,345) | 63 (61,65) |
| 6.9K/cuticle | 8081 (*.*) | 92 (*.*) |
| Ph/cuticle | 725 (585,898) | 92 (83,100) |

*Confidence intervals not attainable

TABLE 2

$RT_{50}$ Values for Third Instar *Heliothis virescens* Leaf Disk Assays at 100,000 PIBs

| Construct Promoter/Signal | $RT_{50}$ (95% Confidence Interval) Expressed in Hours @ 100,000 PIBs (*.*) |
|---|---|
| E2 Wild-type | 108 (*,*) |
| DA26 cuticle | 53 (52,54) |
| DA26/cuticle/hr5 | 54 (53,56) |
| 35k/cuticle | 49 (*,*) |
| 35k/cuticle/hr5 | 49 (*,*) |

*Confidence intervals not attainable

Table 1 shows that the $LD_{50}$ of recombinants with AaIT gene under the control of either a late (6.9K) or very late (polyhedrin) gene promoter is roughly 3–30 times higher than the wild-type virus, whereas the $LD_{50}$ of the recombinant with the AaIT gene under the control of an early (DA26) gene promoter is substantially the same as that of the wild-type virus(this appears to indicate that there is no alteration of virulence of the insect virus). Thus, placement of the AaIT gene under the control of either the late or very late AcMNPV promoters results in a reduction in virus efficacy whereas the use of the DA26 promoter does not. These data are a subset of the data presented in FIG. 1, which depicts the data generated for each promoter tested.

In addition, the data in Table 1 show that the DA26 promoter is much more effective than either the 6.9K (late) or polyhedrin (very late) promoters in improving the speed of action of the recombinant AaIT-expressing AcMNPV viruses. In Table 1, the early promoter (DA26) has a lower $RT_{50}$ value than late promoters (6.9k and polyhedrin) and both late promoters were numerically equivalent.

It is noted that the AcMNPV strain used in the above assays and Example 2 is E2, and all of the AaIT constructs contain the Drosophila cuticle gene signal peptide, which sequence is disclosed in the N. Webb et al. PCT publication.

Example 2

In this example, the above experiment is repeated; however, a different early promoter is tested by replacing the DA26 promoter gene in the above example. Table 2 summarizes a *Heliothis virescens* leaf disk assay where a single dose of 100,000 PIBs (a log higher than in Table 1) was used to generate $RT_{50}$ values.

Table 2, shows that a different early gene promoter from the 35K gene of AcMNPV is as effective as DA26 gene promoter in improving the speed of action of the recombinant AaIT-expressing AcMNPV viruses. Therefore, the effect is not specific to the DA26 promoter.

The data in Table 2 also suggests that there is no difference in the results when an enhancer, such as hr5, is employed in the recombinant insect virus. Table 2 also shows that the close linkage of a transcriptional enhancer element (the hr5 element) is not required in the recombinant virus for an early promoter (in this case the 35K promoter) that requires such elements for maximal activity in a transient gene expression assay. In other words, it does not appear that anything additional has to be done to use enhancer-dependent delayed early genes, such as 35K, in this system since, in all likelihood, the enhancer requirement is met by the enhancer elements that naturally reside in the AcMNPV genome.

Example 3

Figure 2:
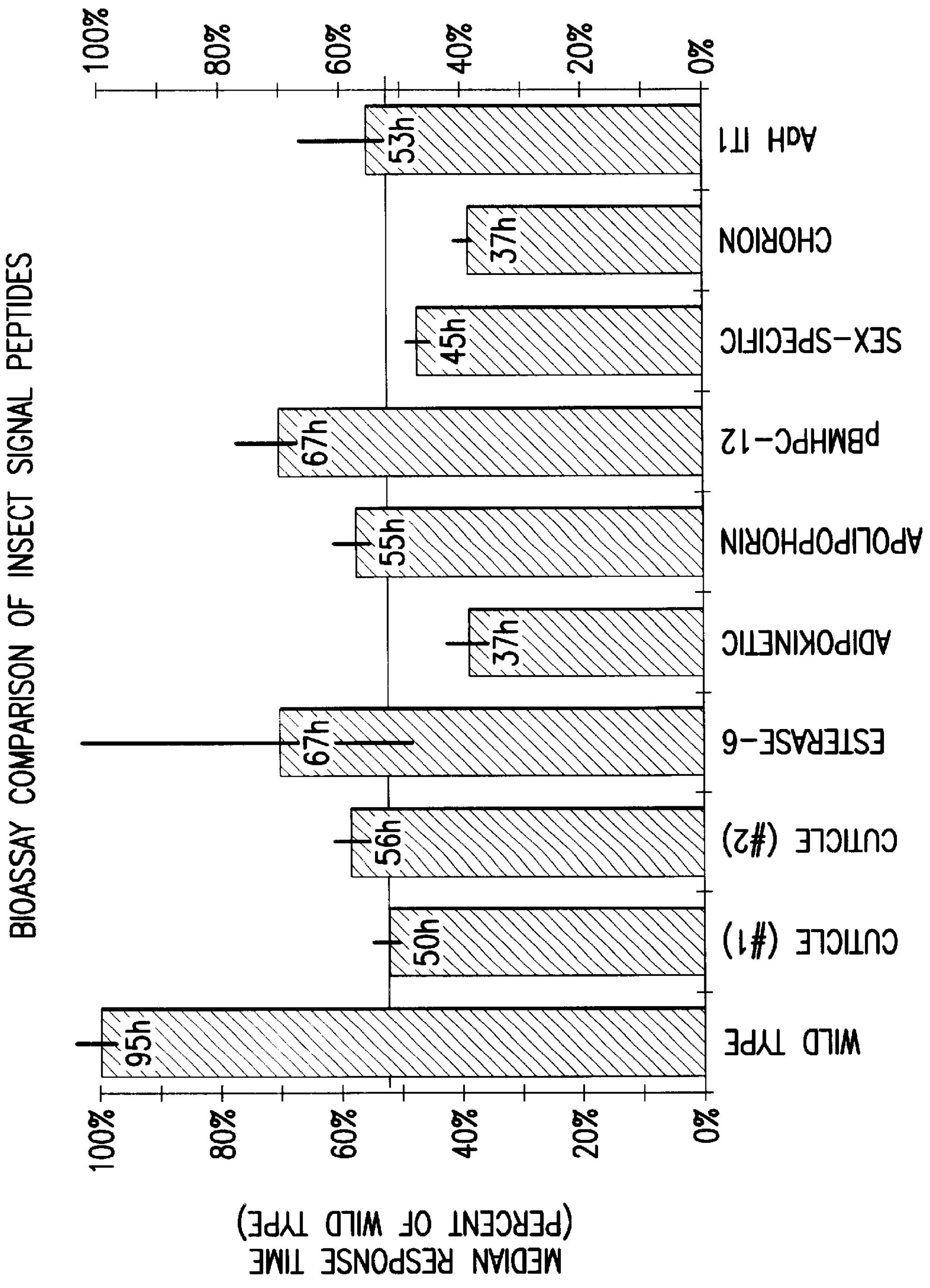
FIG. 2 is a chart of the bioassay conducted in example 2, which compares the effect of changing only the signal peptide for a recombinant insect virus of this invention, using the same early promoter DA26.

In this example, the effect of varying the signal peptide on the enhanced efficacy obtained in using the early promoter is examined. FIG. 2 shows the results of experiments conducted on the variation in median response time as a function of the signal peptide and establishes that the Adipokinetic hormone gene and Chorion gene signal peptides work best. The promoter in all cases is the DA26 promoter. Error bars show 95% confidence intervals.

The AcMNPV strain used in these assays is E2.

Example 4

In this example, the effect of varying the signal peptide and insect virus on the enhanced efficacy obtained in using the early promoter is examined. FIG. 3 is a table excerpted from a report that shows that the DA26 early gene promoter works effectively with several different signal peptides in a variety of AcMNPV backgrounds, including strain E2 (see N. Webb et al.), strain V8 and strain V8EGT (V8 with deletion of egt gene) V8EGT:DA26/ADK-AaIT a more preferred recombinant insect virus.

Example 5

Construction of Transfer Vector NW33.2

The concept of constructing recombinant baculovirus genomes by the directional ligation of viral and foreign DNA segments in vitro is predicated on (1) the identification of two or more restriction endonucleases that fail to cut the DNA genome of the baculovirus under study, and (2) the insertion of a synthetic linker containing these sites into a defined location in the baculovirus genome by conventional methods. In some cases, it may be possible to use an enzyme which cuts the viral genome infrequently if the recognition site(s) can be destroyed by site-directed mutagenesis. Optimally, the restriction enzymes should not only have different recognition sequences, but should also (upon cleavage of a susceptible DNA molecule) produce termini that are not readily joined to each other by T4 DNA ligase in vitro. These criteria ensure that the inserted DNA fragment will be joined to the viral DNA in a predefined orientation. Viruses which have been genetically modified to incorporate these special design features are referred to as direct ligation virus vectors.

Two restriction endonucleases are known to meet these criteria for the *Autographa californica* NPV (AcMNPV) strain E2 genome. Kitts et al. (5) show that there are no recognition sites for restriction endonuclease Bsu 36I in the DNA genome of the C6 strain of AcMNPV. This site is also not present in the DNA genome of AcMNPV strain E2.

Figure 5A:
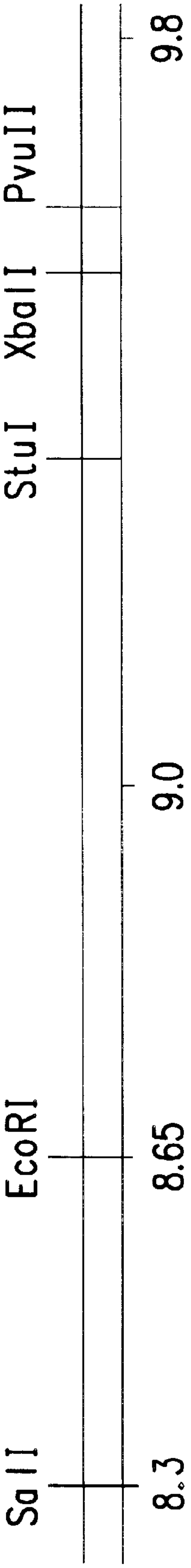
FIG. 5A depicts a schematic representation of the egt gene region, which shows key restriction sites between map units 8.3 and 9.8 in the AcMNPV genome.
Figure 5B:
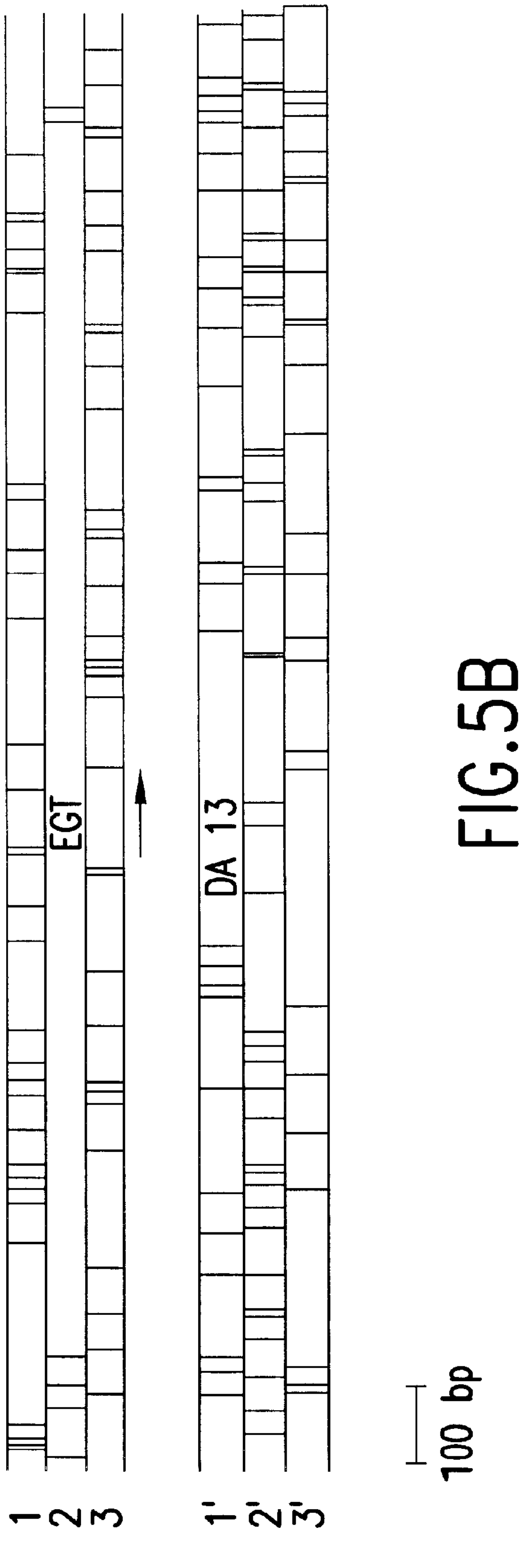
FIG. 5B depicts the organization of open reading frames in the three forward (1, 2, 3) and three reverse (1', 2', 3') reading frames of the AcMNPV genome between map units 8.3 and 9.8. The large open reading frame in frame 2 marks the position of the protein coding region of the egt gene.

Bsu 36I recognizes and cleaves (↓) the DNA sequence CC↓TNAGG. Those skilled in the art will recognize that numerous isoschizomers of Bsu 36I are known, including Eco 81I, Mst II, Cvn I and Sau I, to name a few. As shown in FIG. 5, the Bsu 36I recognition sequence contains two of the four least abundant trinucleotide sequences (AGG and CCT) found in a portion of AcMNPV DNA. Moreover, based on this frequency data one would expect that palindromic restriction sites based on the CCT and AGG trinucleotides (e.g., the Bsu 36I site) would be among the least abundant in the AcMNPV genome. A similar analysis of tetranucleotide sequence frequencies (FIG. 3 of PCT/US94/06079) can be used to identify potential non-cutting enzymes among those restriction endonucleases that recognize 8 bp palindromic sequences. Of the five predicted least abundant classes of palindromic 8-mers, only one class (built on the CCTG and CAGG tetranucleotides) contains the recognition site of a known restriction endonuclease. This enzyme, Sse 8387I, recognizes the sequence CCTGCA↓GG and is the second known enzyme which does not cut the genomic DNA of AcMNPV strain E2. Interestingly, the recognition sequence for Sse 8387I also has the same general sequence pattern (CCT[$N_x$]AGG) as Bsu 36I (where x=1–5). Those skilled in the art will recognize that the frequency data presented in FIGS. 2 and 3 of PCT/US94/06079 can be used to estimate the likelihood that other enzymes, including those with non-palindromic recognition sequences, might be useful for introducing unique recognition sites into the viral genome.

Based on the identification of Bsu 36I and Sse 8387I as enzymes that can be used to prepare direct ligation virus vectors for the E2 strain of AcMNPV, two complementary oligonucleotides (oligo 32 and oligo 33) containing the recognition sites for these enzymes are chemically synthesized and incorporated into transfer vectors that can be used to insert the sites by a conventional method into predefined locations in the AcMNPV genome. The sequences of these oligonucleotides are:

Oligo 32:5'-CCTCAGGGCAGCTTAAGGCAGCGGACCGGCAGCCTGCAGG-3' (SEQ ID NO:1)

Oligo 33:5'-CCTGCAGGCTGCCGGTCCGCTGCCTTAAGCTGCCCTGAGG-3' (SEQ ID NO:2)

In their double-stranded (annealed) configuration, these two oligonucleotides constitute the "Bsu-Sse linker". To anneal the linker, 100 pmol each of oligonucleotides 32 and 33 are diluted into 20 μl of a buffer containing 10 mM Tris-HCl (pH 7.5), 100 mM NaCl and 1 mM EDTA. The mixture is then heated to 78° C. for 10 minutes, transferred to 65° C. and incubated for 20 minutes, and then slow cooled to room temperature.

Figures 4A, 4B:
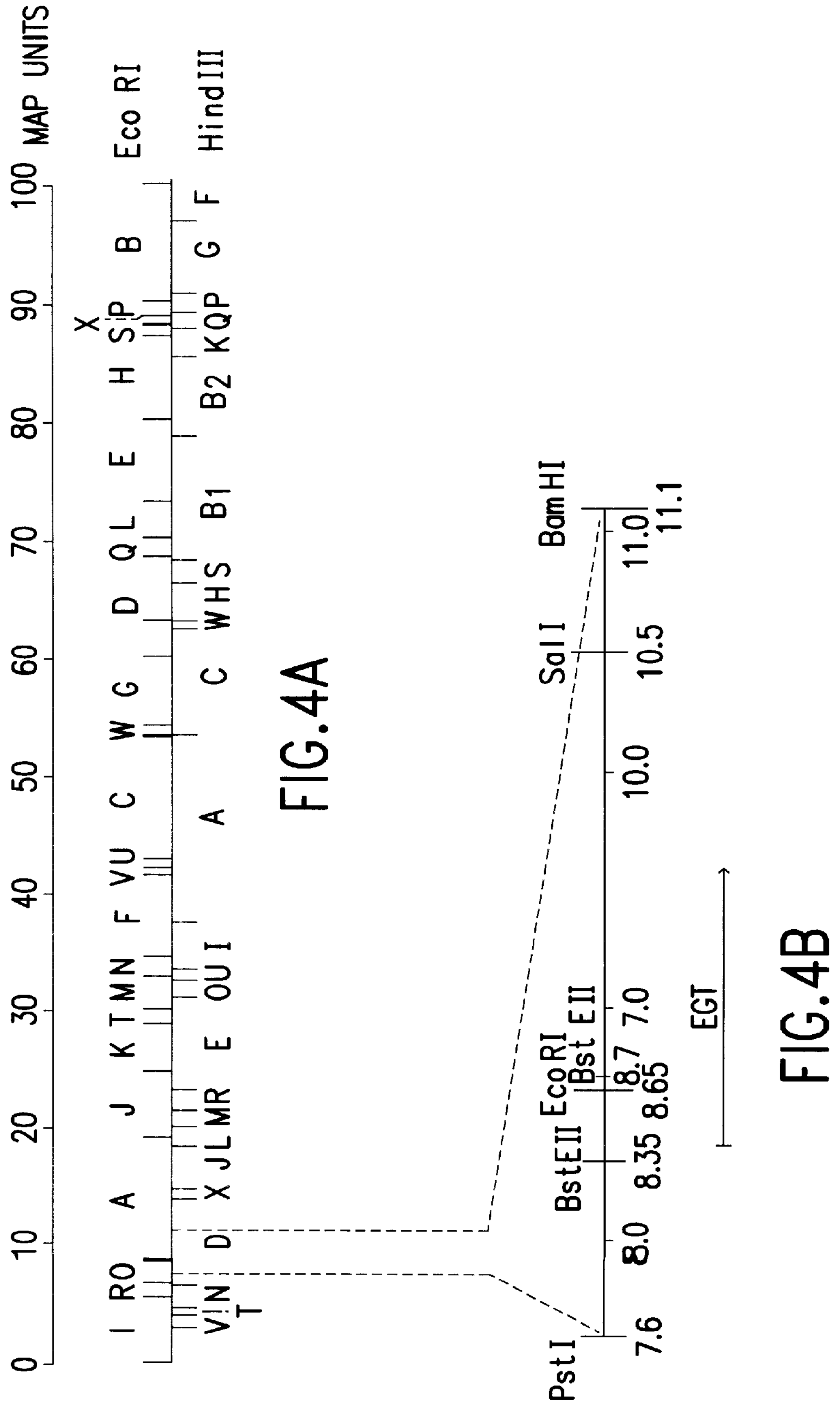
In FIG. 4A the entire AcMNPV genome is presented in map units and as Eco RI and Hind III restriction maps.
FIG. 4B depicts a more detailed map of the region located between map units 7.6 and 11.1 and shows the location of the egt gene.

One site in which the Bsu-Sse linker is inserted is the Eco RV restriction enzyme recognition site (GAT↓ATC) located 92 bp upstream of the translation initiation codon of the AcMNPV polyhedrin gene. This site is frequently used as a site for foreign gene insertion to produce recombinant viruses that are genetically stable and capable of producing large quantities of recombinant protein (11,12). To construct a plasmid in which the Eco RV site of interest is the only Eco RV site present, the approximately 7 kb AcMNPV Eco RI "I" fragment, which contains the polyhedrin gene, is inserted into the unique Eco RI site of pUC19. One of the resulting clones identified as containing the Eco RI "I" fragment is designated NW32.3. To insert the Bsu-Sse linker into the unique Eco RV site of NW32.3, 0.3 pmol of NW32.3 DNA are linearized by digestion with Eco RV and ligated to five pmol of the non-phosphorylated double-stranded linker in a volume of 10 microliters. Excess linker is removed by electrophoresing the ligation mixture on a 1% low melt agarose (BioRad, Richmond, Calif.) gel and isolating the 10 kb DNA band. Approximately one-tenth of this DNA is used to transform competent *E. coli* strain HB101 cells. One of the resulting plasmids, designated NW33.2, is sequenced to confirm the integrity and orientation of the Bsu-Sse linker (FIG. 4 of PCT/US94/06079).

Example 6

Construction of the Direct Ligation

Virus Vector 6.2.1

A recombinant virus containing the Bsu-Sse linker at the Eco RV site upstream of the polyhedrin gene is produced by homologous DNA recombination in cultured Sf9 cells co-transfected with the transfer vector NW33.2 and VL941-500β-gal viral DNA. VL941-500β-gal is a derivative of the E2 strain of AcMNPV in which a part of the polyhedrin gene has been substituted with a segment of DNA that contains the *E. coli* β-galactosidase gene (13). As such, VL941-500β-gal is unable to produce occlusion bodies (polyhedra) and is phenotypically occlusion-negative ($occ^-$). Since the virus formed by homologous DNA recombination between NW33.2, which contains a functional polyhedrin gene, and VL941-500β-gal is expected to be occlusion-positive ($occ^+$), this trait is used to identify potential recombinants.

VL941-500β-gal viral DNA is prepared from extracellular virus obtained from Sf9 cells infected with VL941-500β-gal virus. Two micrograms of NW33.2 plasmid DNA and 1 μg of VL941-500β-gal viral DNA are cotransfected into Sf9 cells by the calcium phosphate coprecipitation method. Cell supernatants are collected 5 days after transfection and $occ^+$ viruses are isolated by three rounds of plaque purification. One $occ^+$ plaque, designated 6.2.1, is used to infect $1\times10^6$ Sf9 cells to produce a Passage 1 (P1) virus stock.

The presence of the Bsu-Sse linker in the 6.2.1 viral DNA is verified by PCR analysis of extracellular virus particles using as primers oligo 32 (see Example 5) and "PVLReverse", which anneals to the viral DNA approximately 320 bp downstream of the site of insertion of the Bsu-Sse linker. PVLReverse:

5'-GGATTTCCTTGAAGAGAGTGAG-3' (SEQ ID NO: 3)

Virus is prepared for PCR analysis essentially as described by Malitschek and Schartl (14). Four microliters of the P1 virus stock is first digested for one hour at 55° C. with 200 μg/ml pronase in a 25 μl reaction containing 1×Buffer A (10 mM Tris (pH 8.3), 50 mM KCl, 0.1 mg/ml gelatin, 0.45% Nonidet™ P40 (Shell Oil Co.), and 0.45%. Tween™ 20 (ICI Americas)). The pronase is then inactivated by heating to 95° C. for 12 minutes. For PCR the pronase-treated virus is mixed with 50 pmol of each of the two oligonucleotide primers in a 50 μl reaction containing 200 μM dNTPs (this is a mixture of nucleotides that contains 200 μM each of dATP, dGTP, dCTP and dTTP), 1–5 mM $MgCl_2$, 1×Buffer A and 2.5 units AmpliTaq™ DNA polymerase (Perkin-Elmer Cetus, Norwalk, Conn.). The sample is subjected to 25 cycles of amplification, each consisting of 1 minute at 94° C. (denaturation step), 1.5 minutes at 55° C. (annealing step), and 2.5 minutes at 72° C. (extension step). The 25 cycles are followed by a 7 minutes extension step at 72° C. One-fifth of the reaction mix is electrophoresed on a 1.8% agarose gel to confirm the presence of the 320 bp amplification product.

Viral DNA is isolated from the 6.2.1 extracellular virus and further characterized by restriction enzyme analysis. Digestion with Eco RI, Bsu 36I, and Sse 8387I is used to confirm the presence of the unique Bsu 36I and Sse 8387I sites in the Eco RI "I" fragment of 6.2.1.

Example 7

Construction of p74-Deficient Direct Ligation

Virus Vector A4000

A direct ligation virus vector incorporating the Bsu-Sse linker (Example 5) into the p74 gene of AcMNPV is produced by conventional methods using a transfer vector which contains sufficient viral DNA sequences to ensure efficient homologous recombination with wild-type AcMNPV DNA. Unlike the 6.2.1 direct ligation virus vector, in which the Bsu-Sse linker is incorporated into an untranslated region of the genome, the Bsu-Sse linker in the current example is inserted into the viral genome in a manner which is intentionally designed to disrupt the integrity of the p74 open reading frame. This results in the formation of a p74-defective virus which produces occlusion bodies that are not orally infectious.

FIG. 5 of PCT/US94/06079 shows the general scheme for assembling the transfer vector used to construct the p74 deficient direct ligation virus vector. The approximately 9.9 kb Bst EII "E" fragment, which contains the p74 gene, is isolated from AcMNPV viral DNA and inserted into a plasmid vector. An approximately 1200 bp Xho I/Hpa I fragment encoding amino acids 24–429 of the p74 protein is replaced with a polylinker containing the Bsu-Sse linker to produce the Δp74-1 transfer vector. The transfer vector Δp74-1 is comprised of 4750 bp of 5' flanking sequences, residues +1–+69 of the p74 open reading frame, a 64 bp polylinker (which includes the 40 bp Bsu-Sse linker sequence), p74 gene sequences from bp +1287 to the termination codon at +1937 (see FIG. 5 of PCT/US94/06079), followed by 1796 bp of 3' flanking sequences. Samples of an *E. coli* strain HB101 harboring this transfer vector have been deposited by applicants' assignee with the American Type Culture Collection, 12301 Parklawn Drive, is Rockville, Md. 20852, U.S.A., and have been assigned ATCC accession number 68988.

A recombinant virus containing the Bsu-Sse linker inserted into a mutated p74 open reading frame is produced by homologous recombination in cultured Sf9 cells co-transfected with Δp74-1 and wild-type AcMNPV (strain E2) viral DNA. The desired recombinant virus is identified by PCR using one oligonucleotide that is specific for the polylinker sequence in the deleted gene (location denoted by leftward arrow in FIG. 5 of PCT/US94/06079) and a second oligonucleotide that is specific for the 3' end of the p74 gene coding region (location denoted by rightward arrow in FIG. 5 of PCT/US94/06079). Samples of this virus, which is designated AcMNPV strain A4000, have been deposited by applicants' assignee with the American Type Culture Collection, 12301 Parklawn Drive, Rockville, Md. 20852, U.S.A., and have been assigned ATCC accession number VR 2373.

Example 8

Construction of Bsp MI-based Modular Expression

Vectors NW44.1 and NW46.50

To utilize the special design features of direct ligation virus vectors, the termini of the DNA fragment to be inserted into the viral genome should be compatible (i.e., readily ligated by T4 DNA ligase) with the termini formed by double digestion of the direct ligation vector with the two uniquely cutting restriction enzymes. FIG. 6 of PCT/US94/06079 displays an example of an expression vector design that is intended for use with a direct ligation virus vector such as AcMNPV strains 6.2.1 or A4000. In this example, the Bsu 36I and Sse 8387I recognition sites flank the ends of a tripartite expression cassette that is composed of the following modules: (1) a promoter module, which is used to regulate gene transcription; (2) a polylinker module, which facilitates insertion of the heterologous DNA sequences whose expression is desired; and (3) a 3' untranslated region (3' UTR), which provides a site for primary transcript processing and polyadenylation. The region bounded by the outermost Bsu 36I and Sse 8387I sites is defined as the virus insertion module. The internal Sse 8387I site marked with an asterisk in the polylinker module in FIG. 6 of PCT/US94/06079 is destroyed when the Bsp MI site is used to insert heterologous gene sequences into the modular expression vector. This internal site is eliminated in the pMEV series of vectors described in Example 5. Similarly, the internal Bam HI site marked with an asterisk in FIG. 6 of PCT/US94/06079 is not required and is also eliminated in the pMEV series of vectors.

Following insertion of the desired heterologous gene sequences into the polylinker module, the virus insertion module is excised from the plasmid vector by double digestion with Bsu 36I and Sse 8387I and inserted by DNA ligation in vitro into a Bsu 361I Sse 8387I double cut direct ligation virus vector, such as AcMNPV strains 6.2.1 or A4000.

The design depicted in FIG. 6 of PCT/US94/06079 has two additional features worth noting. The first is the presence of Stu I recognition sites at both ends of the tripartite expression cassette. If the heterologous gene sequences inserted into the polylinker module do not contain Stu I sites, the orientation of the entire expression cassette can be reversed in the virus insertion module by digesting the plasmid with Stu I and religating the pieces. The second feature is designed to facilitate the fusion of an exogenous open reading frame (beginning with a suitable translation initiation codon, such as ATG) with the 3' terminus of a natural or synthetic 5' untranslated region (5' UTR), such that no extraneous linker sequences are introduced between the 3' terminus of the 5' UTR and the initiation codon. This is accomplished by the precise placement of a Bsp MI recognition site near the 5' terminus of the polylinker module. Bsp MI belongs to a class of Type II restriction endonucleases that cuts both strands of the DNA duplex at sites which lie outside (and on the same side) of its recognition sequence. Moreover, the cuts in each strand are staggered in such a way that the ends of the fragments have 5' protruding termini that can be used as template:primer complexes for a DNA polymerase, such as the Klenow fragment of *E. coli* DNA polymerase I (10):

```
          ↓         -1
......NNNNNNNNNNNNNNNNNNNGCAGGT......
......|||||||||||||||||||||||||......
......NNNNNNNNNNNNNNNNNNNCGTCCA......
                  ↑

                ↓
          Bsp MI digestion
                ↓
```

-continued

```
                           -1
......NNNNNNNNN      NNNNNNNNNGCAGGT......
      |||||||||              ||||||
......NNNNNNNNNNNNNN      NNNNCGTCCA......
                   ↓
   DNA Polymerase I (Klenow fragment) plus dNTPs
                   ↓
              -1          -1
......NNNNNNNNNNNNNN      NNNNNNNNNGCAGGT......
      ||||||||||||||      ||||||||||||||
......NNNNNNNNNNNNNN      NNNNNNNNNCGTCCA......
```

As can be seen from this example, if the Bsp MI site is placed in the correct orientation 4 bp downstream of the 3' terminus of the 5' UTR (underlined nucleotides shown above), one DNA end produced by this process corresponds exactly to the 3' end of the 5' UTR. The 5' UTR is then joined directly to a blunt ended-fragment whose sequence begins with the ATG (or other) initiation codon of the desired open reading frame. As described below, such fragments are easily prepared by PCR techniques. By convention, the 3' terminus of the 5' UTR sequence is designated as position −1 and is used as the landmark for all numerical references in the virus insertion module. In all of the vectors described herein, the 5' UTR is incorporated as part of the promoter module and has the complete nucleotide sequence of the 5' UTR naturally associated with the promoter in that module.

The scheme for constructing Bsp MI-based modular expression vectors containing the AcMNPV 6.9K gene promoter and 3' UTR is illustrated in FIG. 7 OF PCT/US94/06079. The 6.9K gene is a "late" gene that encodes a small arginine rich DNA-binding protein used for packaging viral DNA into nucleocapsids (28,29). The 5' and 3' non-coding sequences flanking the 6.9K open reading frame are isolated by PCR amplification using the AcMNPV Hind III "H" fragment as template. The oligonucleotide primers used for the amplification reactions are each composed of two functional regions. The 5' portion of each oligonucleotide is not homologous to the AcMNPV template and is used to incorporate specific restriction sites into the final PCR product. The 3' portion of each oligonucleotide is homologous to sequences in the AcMNPV genome that define one of the termini of the amplified region.

Figure 8:
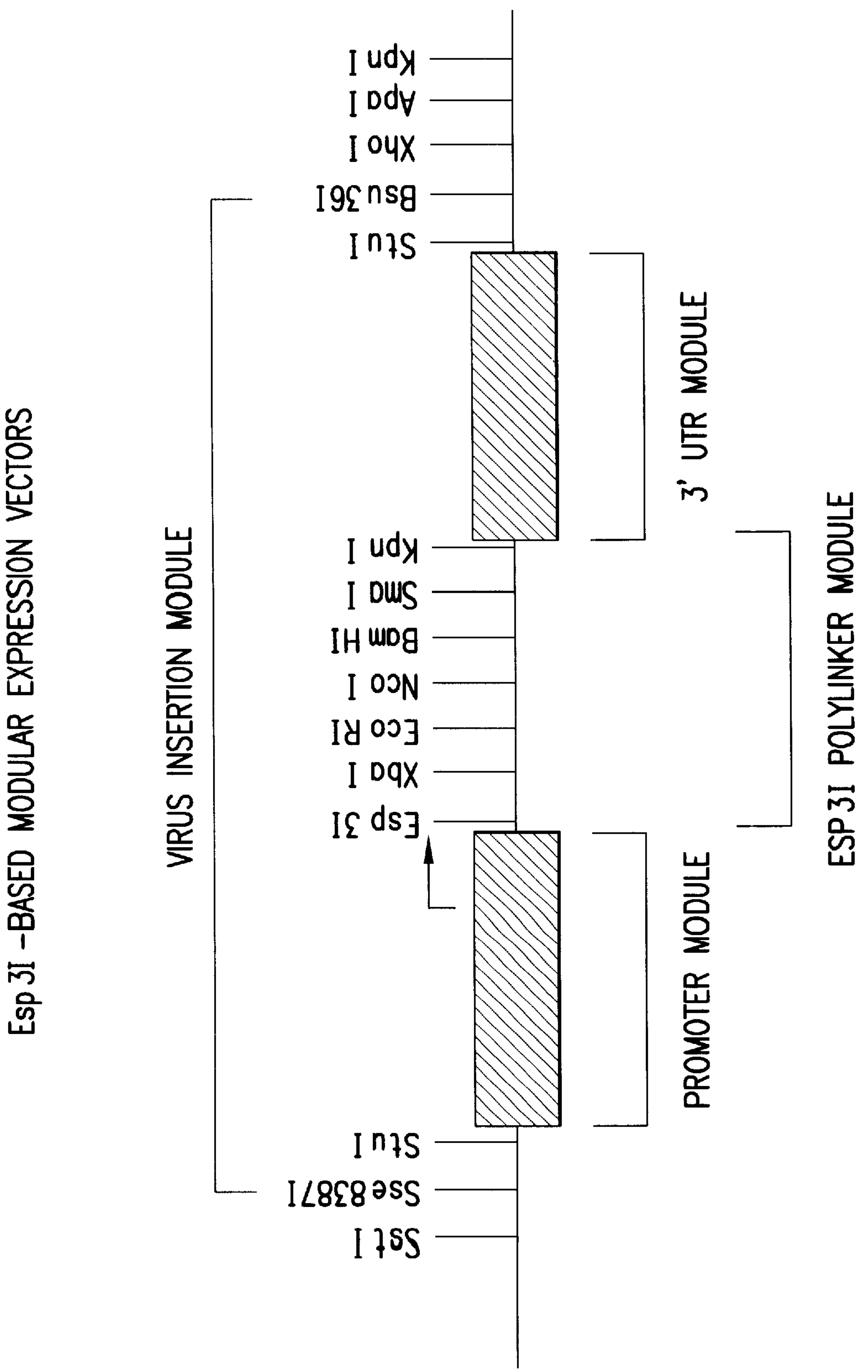

The oligonucleotides used for PCR amplification of the module containing the 6.9K gene promoter and 5' UTR are NW oligo 1, which anneals to the (−) strand approximately 200 bp upstream of the 6.9K translation initiation codon and contains Xho I, Bsu 36I, and Stu I recognition sites, and PD oligo 23, which anneals to the (+)strand immediately upstream of the 6.9K translation initiation codon and contains Bam HI and Bsp MI recognition sites. The sequences of these primers and of the PCR amplification product are presented in FIG. 8 of PCT/US94/06079.

The oligonucleotides used for PCR amplification of the 6.9K gene 3' UTR are NW oligo 2, which anneals to the (−) strand immediately downstream from the translation stop codon of the 6.9K open reading frame and contains recognition sites for Xba I, Eco RI, Nco I, Bam HI, Sma I and Kpn I, and NW oligo 3, which anneals to the (+) strand approximately 200 bp downstream of the translation stop codon and contains recognition sites for Stu I, Sse 8387I and Sst I. The sequences of these primers and of the PCR amplification product are presented in FIG. 9 of PCT/US94/06079.

The amplification reactions for the 6.9 K promoter module and 3' UTR module are conducted in separate GeneAmp tubes (Perkin-Elmer Cetus, Norwalk, Conn.) according to the following procedure. Fifty picomoles of the appropriate primer pair (i.e., 50 pmol of each oligonucleotide) are combined with 250 pg of AcMNPV Hind III fragment “H” DNA (see FIG. 4 of PCT/US94/06079) in a 50 $\mu$l reaction mixture containing 200 $\mu$M dNTPs, 1.5 mM $MgCl_2$ 1×Buffer A and 2.5 units AmpliTaq™ DNA polymerase (Perkin-Elmer Cetus, Norwalk. Conn.). The samples are first subjected to 5 rounds of amplification consisting of 1 minute at 94° C. (denaturation step), 1.5 minutes at 45° C. (annealing step), and 2.5 minutes at 72° C. (extension step). This is followed by 20 cycles consisting of 1 minute at 94° C. (denaturation step), 1.5 minutes at 60° C. (annealing step), and 2.5 minutes at 72° C. (extension step). The last extension step is extended an additional 7 minutes.

The amplification products are extracted once with chloroform, once with phenol: chloroform, and then precipitated with ethanol. The fragment containing the presumptive promoter module is digested with Xho I and Bam HI (see FIG. 8 of PCT/US94/06079) and the fragment containing the presumptive 3' UTR module is digested with Xba I and Sst I (see FIG. 9 of PCT/US94/06079). Each of the desired fragments is then isolated by electrophoresis on a 1.8% low melt agarose gel. The promoter fragment is inserted into the polylinker of Bluescript $SK^+$ (Stratagene, La Jolla, Calif.) between the Xho I and Bam HI sites, and the 3' UTR fragment is inserted into the polylinker of a separate Bluescript $SK^+$ plasmid between the Xba I and Sst I sites (see FIG. 7 of PCT/US94/06079). The plasmid identified as containing the 6.9K promoter module is designated NW39.2, while that containing the 6.9K 3' UTR is designated NW41.5. Both NW39.2 and NW41.5 are sequenced to verify the integrity of the 6.9K gene segments and flanking linker sequences.

To construct a complete Bsp MI-based modular expression vector, NW39.2 and NW41.5 are digested with Xba I and Sst I and the fragments are resolved by electrophoresis on a 1.2% low melt agarose gel. The 3.1 kb fragment derived from NW39.2 and the 200 bp fragment derived from NW41.5 are extracted from the gel and ligated together. A clone containing the desired promoter, polylinker and 3' UTR modules is identified by restriction enzyme analysis and is designated NW44.1.

To obtain a vector in which the expression cassette has the opposite orientation within the virus insertion module, NW44.1 is first digested with Stu I. The 2.9 kb Stu I fragment is purified by gel electrophoresis, dephosphorylated to prevent self-litigation, and re-ligated to the 450 bp NW44.1 Stu I fragment containing the expression cassette. A clone containing the Stu I insert in the opposite orientation relative to NW44.1 is identified by restriction enzyme analysis and designated NW46.50.

Example 9

Construction of Esp 3'-based Modular Expression Vectors pMEVI, pMEV2, pMEV3 and pMEV4

The modular expression vectors pMEV1, pMEV2, pMEV3 and pMEV4 are constructed from NW46.50 by substituting the promoter-containing Pst I/Xba I fragment of NW46.50 with Pst I/Xba I-digested fragments containing the AcMNPV DA26 (pMEV1), 6.9K (pMEV2), polyhedrin (pMEV3) and 35K (pMEV4) viral gene promoters. The DA26 and 35K genes are expressed at an early stage in the life cycle of the virus (i.e., before the onset of DNA synthesis) (17,18). As noted earlier, the 6.9K gene encodes a “late” class structural protein, which is expressed after the onset of DNA synthesis (15). The polyhedrin gene belongs to the class of genes that are expressed “very late” in the virus life cycle and encodes the major structural component of the viral occlusion bodies.

Figure 10:
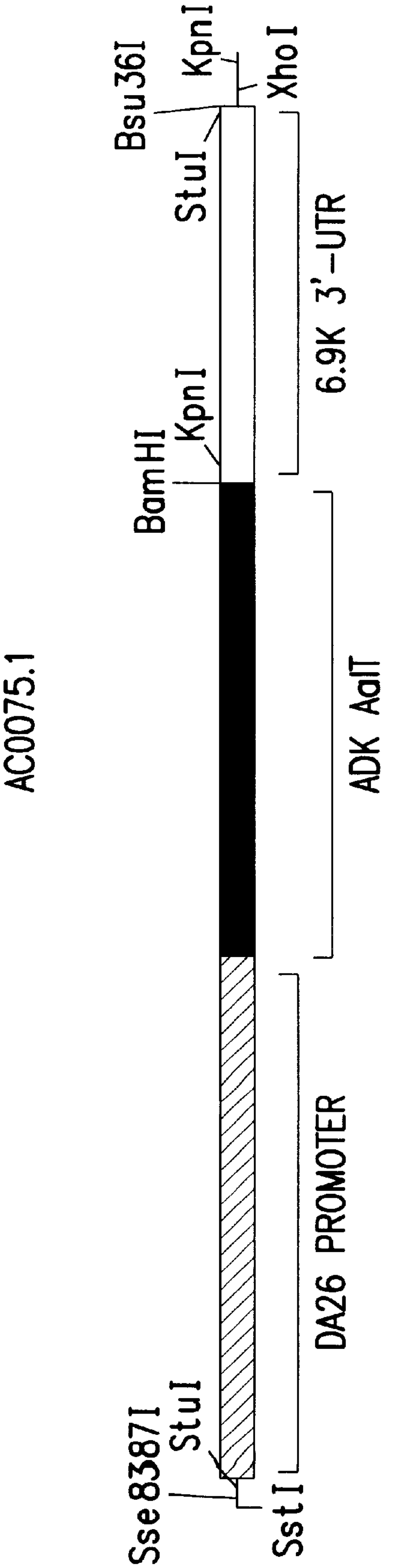

As depicted in FIG. 10 of PCT/US94/06079, the design of the Esp 3I-based vectors is a refinement of the Bsp MI-based model, in which (1) the redundant Bam HI and Sse 8387I sites in the polylinker module are eliminated, and (2) the Bsp MI recognition site is replaced by an Esp 3I site. Esp 3I belongs to the same general class of Type II restriction endonuclease as Bsp MI, in that it cuts outside of its recognition sequence and produces 5' protruding termini that can be filled in by DNA polymerase. Experience indicates, however, that Esp 3I has a more robust activity than Bsp MI and is the preferred enzyme when all other factors permit its use (e.g., when there are no Esp 3I sites in either the promoter module or the 3' UTR module). To use Esp 3I in the manner illustrated earlier for Bsp MI, its recognition site must be placed in the correct orientation 1 bp downstream of the 3' end of the 5' UTR.

As described in Example 8 for the Bsp MI-based vectors, the promoter fragments used in constructing the Esp 3I-based vectors are formed by PCR amplification of cloned viral DNA using promoter-specific pairs of oligonucleotide primers. The primers are designed so that the amplified promoter segments have the following general structure: (1) a 5' terminal 22 bp heteropolymeric synthetic sequence with recognition sites for restriction endonucleases Sst I, Sse 8387I and Stu I (in that order); (2) a segment of viral DNA that extends from a point 100–350 bp upstream of the predominant transcriptional start site of the gene to the 3' terminus of the 5I UTR (i.e., position −1 with respect to the translation initiation codon); and (3) a 3' terminal 23 bp heteropolymeric region with recognition sites for restriction endonucleases Esp 3I and Xba I (in that order). The location and orientation of the Esp 3I recognition site places the cleavage sites between positions −5 and −4 in the (+)strand and between positions −1 and +1 in the (−)strand.

The template used to prepare each promoter, the sequences of the primers and the sequences of the amplified PCR products are shown in FIGS. 11, 12, 13 and 14 of PCT/US94/06079.

For each amplification reaction, 50 pmol of the appropriate primer pair are mixed with 250 pg of template DNA in a 50 $\mu$l reaction mixture containing 10 mM Tris-HCl (pH.8.3), 50 mM KCl, 1.5 mM $MgCl_2$, 200 $\mu$M dNTPs, 100 $\mu$g/ml gelatin and 2.5 units AmpliTaq™ DNA polymerase (Perkin-Elmer Cetus, Norwalk. Conn.). For the DA26, 6.9K and polyhedrin promoter modules, the samples are then subjected to 2 rounds of amplification consisting of 1 minute at 94° C. (denaturation step), 1.5 minutes at 40° C. (annealing step), and 2.5 minutes at 72° C. (extension step). This is followed by 15 cycles of 1 minute at 94° C. (denaturation step), 1.5 minutes at 60° C. (annealing step), and 2.5 minutes at 72° C. (extension step). The last extension step is programmed to run an additional 7 minutes. For the 35K promoter module, the sample is amplified through 25 cycles of 1 minute at 94° C. (denaturation step), 1.5 minutes at 55° C. (annealing step), and 3.0 minutes at 72° C. (extension step). As in other reactions, 7 minutes is added to the last extension step.

Each reaction is terminated by the addition of EDTA to 10 mM and Sarkosyl (sodium N-lauroylsarcosine) to 0.2% (w/v). The products are then extracted once with chloroform, once with phenol:chloroform and precipitated with ethanol. The DNA samples are redissolved in an appropriate buffer and then digested with Pst I (which recognizes the central six basepairs [CTGCA↓G] of the Sse 8387I site) and Xba I. Each presumptive promoter fragment is then purified by gel electrophoresis on a 1.2% low melt agarose gel and ligated to a 3.2 kb Pst I/Xba I vector fragment prepared from NW46.50 (see FIG. 7 of PCT/US94/06079). This fragment contains the polylinker module, 3I UTR module and Bluescript SK+framework of NW46.50. The desired recombinants are identified by restriction enzyme analysis and DNA sequence determination. Representative isolates of each expression vector are designated pMEV1.1 for the DA26 promoter, pMEV2.1 for the 6.9K gene promoter, pMEV3.1 for the polyhedrin gene promoter and pMEV4.1 for the 35K gene promoter. Samples of an *E. coli* strain DH5 harboring plasmid pMEV1.1 (AC0064.1) have been deposited by applicants with the American Type Culture Collection, 12301 Parklawn Drive, Rockville, Md. 20852, U.S.A., on Apr. 13, 1993, and have been assigned ATCC accession number 69275.

Example 10

Construction of Esp 3'-based Modular Expression Vectors Containing the Drosophila hsp70Gene In some cases, it may be advantageous to use an insect cell promoter rather than a viral promoter to direct transcription of a foreign gene in a baculovirus-based expression system. In particular, Morris and Miller (19) report that a Drosophila hsp70 (major heat shock) gene promoter functions at a comparable or better level than the AcMNPV ETL (early) gene promoter in directing expression of a chloramphenicol acetyltransferase (CAT) reporter gene in a variety of insect cell lines. To construct an expression vector that uses an insect cell promoter to control foreign gene expression and that can be used with the direct ligation virus vectors, a DNA segment of *Drosophila melanogaster* DNA containing the hsp70 promoter and 5' UTR is amplified by PCR and substituted into one of the modular expression vectors described above. The sequences of the primers for this reaction and the predicted sequence of the amplified fragment, which contains an Esp 3I site in the presumptive polylinker region, are presented in FIG. 15 of PCT/US94/06079. The procedures for PCR amplification of the hsp70 promoter module, and for inserting this module into an NW46.50-based expression vector are as described in Example 9 for the AcMNPV 35K promoter module. A resulting clone with the desired structure is designated pMEV5.

Example 11

Construction of Esp 3I-based Modular Expression Vectors Containing an Alternative 3' UTR and the hr5 enhancer AcMNPV contains five regions of homologous DNA sequence, designated hr1 to hr5, that are widely interspersed along its genome (20). Each region is 500–800 bp in length and contains variations of several repeated sequence motifs, one of which (IR24) (21) contains an Eco RI recognition site. Functional studies have shown that regions such as hr5 are complex cis-acting regulatory domains that can enhance the transcriptional activity of at least some linked early viral genes (e.g., the 35K gene) by as much as 300- to 1000-fold (22). In addition, recent evidence suggests that the hr elements may also serve as origins for DNA synthesis (23).

The hr5 element lies downstream and immediately adjacent to the AcMNPV 35K gene, and is therefore well suited for use as an alternative 3' UTR module. FIG. 16 of PCT/US94/06079 displays the sequences of two oligonucleotides for the PCR amplification of a segment of the AcMNPV genome that begins just upstream of the 3' terminus of the 35K gene and extends through all six IR24 repeats (marked by the Eco RI sites) of hr5. The conditions used for PCR amplification of the hr5 domain are the same as those described for the amplification of the 35K promoter module in Example 5. After purification, the PCR product is digested with Bam HI and Xho I and the presumptive hr5 enhancer module is isolated on a 1% low melt agarose gel. This module is then ligated with gel purified Bam HI/Xho I vector fragments prepared from each of the Esp 3I-based modular expression vectors described in Examples 9 and 10. The result is a new series of vectors in which the 6.9K gene-derived 3' UTR module is replaced by the hr5 module. Plasmids with the desired structures are identified by restriction enzyme analysis and are designated pMEV1A (with the DA26 gene promoter module), pMEV2A (with the 6.9K gene promoter module), pMEV3A (with the polyhedrin gene promoter module), pMEV4A (with the 35K gene promoter module) and pMEV5A (with the *Drosophila melanogaster* hsp70 promoter module).

Example 12

Construction of Modular Expression Vectors Containing Codon-Optimized or Native Sequence AaIT Genes One application in which the direct ligation technology and the vectors described in Examples 8–11 are particularly useful is the design and optimization of recombinant viral insecticides. These are viruses, especially baculoviruses, whose insecticidal properties have been enhanced by the addition of one or more foreign genes that encode insect-specific toxins (8,9,24); peptide hormones (25) or enzymes (32).

The peptide AaIT, which is found in the venom of the North African scorpion *Androctonus australis*, is an example of such an insect-specific toxin (28). When AaIT is injected into the body cavity of an insect larva, it binds selectively to voltage-sensitive sodium channels and causes a contractile paralysis. Chronic administration of the toxin, which can be achieved by infecting insect larvae with AaIT-producing viruses, is associated with a prolonged state of paralysis and eventual death.

Transfer vectors are constructed for the insertion of AaIT genes into the polyhedrin gene region of AcMNPV. These transfer vectors are derivatives of the published pVL1393 (4) and pVL985 (13) vectors. In one vector, the AaIT coding region is inserted between the Bam HI and Eco RI sites of pVL1393 and has the same nucleotide sequence (SEQ ID NO:45 of PCT/US94/06079) as the coding region of the AaHIT1 cDNA described by Bougis et al. (26), and is used in conjunction with the native nucleotide sequence encoding the native AaIT signal peptide (SEQ ID NO:28 of PCT/US94/06079). In seven other vectors, the AaIT gene is inserted into the Bam HI site of pVL985 and consists of a codon-optimized nucleotide sequence, (nucleotides 49-258 of SEQ ID NO:29 of PCT/US94/06079) for the mature AaIT toxin, which is linked in each vector to a separate codon-optimized sequence for one of seven different insect signal peptides identified below. One such construct, containing the codon-optimized AaIT gene linked to the signal peptide of a Drosophila cuticle gene, is designated pAC0055.1. FIG. 17A of PCT/US94/06079 depicts the region of pAC0055.1 which contains the cuticle signal and AaIT gene inserted into the unique Bam HI site located between residues +34 and +177 of the polyhedrin gene. The ATT sequence at +1 indicates the mutated translation start codon in the parental pVL985 vector. Samples of an *E. coli* strain HB101 harboring the transfer vector pAC0055.1 have been deposited by applicants with the American Type Culture Collection, 12301 Parklawn Drive, Rockville, Md. 20852, U.S.A., and have been assigned ATCC accession number 69166. In an alternative embodiment, the native, rather than codon optimized, nucleotide sequences encoding the seven different insect signal peptides are used.

The toxin coding segments of these transfer vectors are recovered by PCR for subsequent insertion into modular expression vectors. The PCR strategy (FIG. 17A of PCT/US94/06079) and the sequence of the amplified fragment (FIG. 17B of PCT/US94/06079) are exemplified for the Cuticle/AaIT gene. The (+)strand primer used for each reaction is an oligonucleotide of 25–27 bases whose 5' terminus coincides with the ATG translation initiation codon of the gene to be amplified. The specific sequences of the (+)strand primers used to amplify each AaIT gene are listed below, followed by identification of the insect species signal peptide which is the source of the primer used:

5'-ATG AAC TAC GTC GGG CTG GGC CTC ATC-3' (esterase-6 signal from *Drosophila melanogaster*; SEQ ID NO:4, nucleotides 1–27).

5'-ATG TAC AAA CTG ACC GTC TTC CTG ATG-3' (adipokinetic hormone signal from *Manduca sexta*; SEQ ID NO: 5, nucleotides 1–27).

5'-ATG TTC AAG TTC GTG ATG ATC TGC GCC-3' (cuticle signal from *Drosophila melanogaster*; SEQ ID NO: 6, nucleotides 1–27).

5'-ATG GCC GCT AAA TTC GTC GTG GTT CTG-3' (apolipophorin signal from *Manduca sexta*; SEQ ID NO: 7, nucleotides 1–27).

5'-ATG AAA CTC CTG GTC GTG TTC GCC ATG-3' (pBMHPC-12 signal from *Bombyx mori*; SEQ ID NO: 8, nucleotides 1–27).

5'-ATG CGC GTC CTG GTG CTG TTG GCC TGC-3' (sex specific signal from *Bombyx mori*; SEQ ID NO: 9, nucleotides 1–27).

5'-ATG TTC ACC TTC GCT ATT CTG CTC TTG-3' (chorion signal from *Bombyx mori*; SEQ ID NO:10, nucleotides 1–27, except that nucleotide 25 in the primer is a T instead of a C).

5'-ATG AAA TTT CTC CTA TTG TTT CTC G-3' (native signal for AaIT; SEQ ID NO:11, nucleotides 1–25).

The first seven primers are used with a codon optimized gene encoding AaIT (nucleotides 49-258 of SEQ ID NO:29 of PCT/US94/06079); the last primer is used with the native gene encoding AaIT.

The (−)strand primer in each case is the PVLReverse primer (see Example 6), which hybridizes to a common site located about 35–40 bp downstream of the 3' terminus of the AaIT gene (i.e., in the polyhedrin gene). The conditions for the PCR reaction are essentially as described for the 35K promoter module in Example 9. After purification the reaction products are treated with the Klenow fragment of *E. coli* DNA polymerase I in the presence of all four dNTPs to ensure that the PCR products have blunt 5' termini. The 3' terminus of each toxin coding fragment is then defined by digesting the PCR products with either Bam HI (for the codon-optimized AaIT genes) or Eco RI (for the native sequence AaIT gene), and the fragments are purified by electrophoresis on a 1.8% low melt agarose gel. FIG. 17B depicts the complete nucleotide sequence of the PCR amplified codon optimized cuticle/AaIT coding region (SEQ ID NO:29, nucleotides 1258).

To prepare the Esp 3I-based modular expression vectors for toxin gene insertion, each vector is digested with Esp 3' and the resulting 5' protruding termini are filled in by the action of *E. coli* DNA polymerase I (Klenow fragment) in the presence of all four dNTPs. Part of each preparation is then digested with Bam HI (for insertion of the codon-optimized gene fragments) and part is digested with Eco RI (for the native sequence gene fragment). The vector is separated from the liberated polylinker fragment by electrophoresis on a 1% low melt agarose gel and then ligated in separate reactions to the appropriate AaIT-encoding gene fragments. A schematic representation and the complete nucleotide sequence of the virus insertion module designated AC0076.1 formed by inserting the Cuticle/AaIT coding region into pMEV1 (which contains the AcMNPV DA26 promoter) is presented in FIG. 18 of PCT/US94/06079.

Example 13

Preparation of 6.2.1 and A4000 Viral DNAs for Ligation

To prepare the 6.2.1 and A4000 viral DNAs for gene insertion by ligation in vitro, the DNAs are linearized by sequential digestions with Sse 8387I and Bsu 36I, and then separated from the small Bsu-Sse linker fragment by gel filtration chromatography. In a typical preparation, forty micrograms of 6.2.1 or A4000 viral DNA are digested for hours at 37° C. with 100 units of Sse 8387I (Takara Biochemical, Inc., Berkeley, Calif.) in a 250 $\mu$reaction containing 10 mM Tris pH 7.5, 10 mM $MgCl_2$ 1 mM dithiothreitol (DTT), 50 mM NaCl, and 0.01% BSA. The reaction mixture is then adjusted to 100 Mm NaCl and 50 mM Tris HCl, pH 7.9, and the DNA is digested for 2 hours at 37° 'C. with 100 units of Bsu 36I (New England Biolabs, Beverly, Mass.). The reaction is then terminated by adding SDS to a final concentration of 1%(w/v), NaCl to a final concentration of 0.3 M and EDTA to a concentration of 10 mM.

Thereafter, the DNA is chromatographed on a "polyprep" column (BioRad Laboratories, Richmond, Calif.) containing a 2 ml bed volume of Sephacryl-300 (Pharmacia, Piscataway, N.J.) equilibrated with 10 mM Tris-HCl (pH8.0), 1 mM EDTA, 0.1% SDS, and 0.3 M NaCl. Twelve 150 $\mu$l fractions are collected. Ten microliters of each fraction are analyzed by gel electrophoresis to identify fractions containing the viral DNA. These fractions are pooled, extracted once with phenol:chloroform, and the viral DNA is then precipitated with ethanol. The DNA is resuspended in TE (10 mM Tris-HCl (pH 8.0), 1 mM EDTA) at a concentration of 0.2–1 $\mu$g/$\mu$l and stored at 4° C. To determine if the viral DNA has been linearized completely, an aliquot is digested with Eco RI and analyzed by gel electrophoresis. Viral DNA exhibiting a 7 kb Eco RI fragment has not been digested completely with Bsu 36I and Sse 8387I and is not used.

Example 14

Insertion of Foreign DNA into the Direct Ligation Virus Vector 6.2.1 by Ligation In Vitro The efficiency of obtaining recombinant viruses by ligating foreign DNA in vitro into the unique Bsu 36I/Sse 8387I cloning site of linearized 6.2.1 viral DNA is demonstrated with the 2.9 kb Bsu 36I/Sse 8387I fragment of NW44.1, which consists mainly of DNA sequences from the Bluescript cloning vector (FIG. 7 of PCT/US94/06079).

This fragment is purified by digesting plasmid NW44.1 sequentially with Sse 8387I and Bsu 36I and then separating the digestion products on a 1% low melt agarose gel containing 40 mM Tris-acetic acid (pH 7.8), 1 mM EDTA and 0.5 μg/ml ethidium bromide. After electrophoresis, a gel slice containing the 2.9 kb Bsu 36I/Sse 8387I vector fragment is carefully excised. To extract the DNA from the gel, the slice is diluted with 3 volumes of a buffer containing 20 mM Tris-HCl (pH 7.5), 0.4 M sodium acetate and 1 mM EDTA. The mixture is heated to 65° C. until the gel slice is melted, then cooled to 37° C. and extracted with an equal volume of watersaturated phenol (equilibrated to room temperature). After extraction, the phases are separated in a microfuge (15,000 rpm for 3 minutes at room temperature) and the phenolic phase is removed. The aqueous phase and interface material are re-extracted with water-saturated phenol until little or no precipitate remains at the interface. The aqueous phase is then removed and the 2.9 kb DNA fragment is concentrated by ethanol precipitation.

One-half microgram of Bsu 36I/Sse 8387I linearized 6.2.1 viral DNA (see Example 9) is mixed with approximately 12 mg of the Bsu 36I/Sse 8387I fragment of NW44.1 in a 5 μl reaction mixture containing 25 mM TrisHCl (pH 7.6), 5 mM $MgCl_2$ 1 mM ATP, 1 mM DTT, 5% (w/v) polyethylene glycol-8000, and 0.5 units T4 DNA ligase (Gibco-BRL, Gaithersburg, Md.). After an overnight incubation at 16° C. the entire ligation reaction is used to transfect Sf9 cells.

For transfection, $1.5\times10^6$ Sf9 cells are plated in one well of a 6-well cluster dish. After the cells have attached, the cell culture medium is replaced with 0.375 ml Grace's Insect cell culture medium (27). The contents of the ligation reaction are mixed with 0.375 ml of transfection buffer (25 mM HEPES (pH 7.1), 140 mM NaCl, 125 mM $CaCl_2$) and then added dropwise to the plated cells. A separate well is similarly treated with one half microgram of linearized (unligated) 6.2.1 viral DNA to provide a negative control. The cells are incubated with the DNA for 4 hours at 27° C., washed once with 2 ml of Grace's Insect medium supplemented with 0.33% (w/v) lactalbumin hydrolysate, 0.33% (w/v) TC yeastolate, 0.1% (v/v) Pluronic™ F-68 (Gibco BRL, Gaithersburg, Md.) and 10% (v/v) fetal bovine serum (complete TNM-FH medium), and then incubated for 2 hours at 27° C. with 2 ml of complete TNM-FH. The cells are then harvested and one-tenth of the total culture (approximately 150,000 transfected cells) is mixed with $2\times10^6$ untreated Sf9 cells. The mixture is plated on a 6 cm tissue culture dish and the attached cells are carefully overlaid with 4 ml complete TNM-FH medium supplemented with 1.5% SeaPlaque™ agarose (FMC BioProducts, Rockland, Me.), 100 units/ml penicillin G and 100/μ/ml streptomycin sulfate. Since the cells are harvested 6 hours after transfection (i.e., before the production of extracellular virus), viral plaques are produced only by those cells which have taken up infectious viral DNA. Hence, the number of plaques on each plate provides a direct measure of the efficiency of the transfection event.

Five days after plating, the dishes are scanned for the presence of $occ^+$ plaques. For one experiment, fifteen plaques are observed on a plate containing linearized and unligated 6.2.1 viral DNA (the negative control). Sixty-nine plaques are observed on the plate containing 6.2.1 viral DNA ligated to the NW44.1 Bsu 36I/Sse 8387I fragment. Eighteen of these plaques are picked at random for further analysis.

The plaques are transferred to individual wells of a 48-well cluster dish containing $7.5\times10^4$ Sf9 cells and 0.5 ml complete TNM-FH media. After 5 days, the extracellular virus is harvested from the wells and analyzed by PCR (see Example 6) for the presence of the NW44.1-derived Bluescript sequences in the viral genome. The primers used for PCR are PVLReverse (see FIG. 4 of PCT/US94/06079), which anneals to the viral DNA approximately 320 bp downstream of the site of insertion of the Bsu-Sse linker in 6.2.1 (Example 6), and Bluescript "sequencing primer", which corresponds to the sequence on Bluescript SK+DNA approximately 100 bp upstream of the insertion of the Bsu-Sse linker:

Bluescript sequencing primer: 5'-CCATGATTACGCCAAGCGCG-3' (SEQ ID NO:12)

With this primer set, a recombinant virus containing the NW44.1-derived Bluescript sequences yields a PCR product of approximately 400 bp in length, whereas no specific PCR products are formed with non-recombinant 6.2.1 viral DNA. The conditions for PCR are as described in Example 2. One-fifth of the PCR reaction is analyzed on a 1.8% agarose gel. All of the test samples contain the predicted 400 bp amplification product, indicating that each of the eighteen randomly picked viruses contains the desired insert. This result not only demonstrates the feasibility of the direct ligation approach, but also shows that the efficiency of recombinant virus recovery is very high.

Samples of an isolate designated A4001 (containing the cuticle/AaIT gene under the control of the DA26 promoter inserted into the A4000 direct ligation virus vector) and of an isolate designated A1001 (containing the cuticle/AaIT gene under the control of the DA26 promoter inserted into the 6.2.1 direct ligation virus vector) have been deposited by applicants with the American Type Culture Collection, 12301 Parklawn Drive, Rockville, Md. 20852, U.S.A., on Apr. 13, 1993, and have been assigned ATCC accession numbers VR-2405 (for A4001) and VR-2404 (for A1001).

Example 15

Construction of Strain V8vEGTDEL

To construct a recombinant AcMNPV (strain V8; ATCC VR-2465) virus incapable of expressing a functional eqt gene, a DNA fragment containing the AcMNPV eqt gene and extending from the Pst I site at m.u. 7.6 to the Bam HI site at m.u. 11.1 of the AcMNPV genome is first inserted into pUC19 (Sigma Chemical Co., St. Louis, Mo.) between the Pst I and Eco RI sites of the pUC19 polylinker (see FIG. 1 for a schematic restriction map of the AcMNPV genome and the placement of sites with respect to the eqt gene). The Bam HI end of the AcMNPV DNA fragment and the Eco RI end of the pUC19 polylinker are both filled in by treatment with T4 DNA polymerase prior to fragment ligation so as to facilitate the fragment joining in such as way that the Eco RI site in the polylinker region of the product is destroyed. The resulting plasmid is designated pUCBCPsB.

Plasmid pUCBCPsB is cleaved with restriction endonuclease Xba I (see FIG. 5 for the placement of these sites within the eqt gene) and treated with T4 DNA polymerase to fill in the overhanging end at the Xba I cleavage site. The linearized plasmid is then cleaved with Eco RI and the small Xba I/Eco RI fragment is discarded. The *Escherichia coli* lacZ gene, excised from pSKS104 (31) with Eco RI and Aha III, is then inserted between the Eco RI and filled in Xba I sites. The resultant plasmid is designated pEGTZ. In this plasmid, the inserted lacZ gene is in frame with the preceding eqt coding sequences. Alternatively, the plasmid pEGTDEL is constructed by simply ligating the Eco RI and Xba I sites together (after both sites have been blunt-ended) without inserting any sequences between them.

Plasmid pEGTZ is then cotransfected with AcMNPV V8 DNA into SF cells as described in Summers and Smith (6) This procedure allows for homologous recombination to take place between sequences in the viral and plasmid DNAs, resulting in replacement of the viral eqt gene with the eqt-lacZ gene fusion from pEGTZ. Because the remaining eqt coding sequence is in frame with the lacZ sequences, the resulting virus (designated V8vEGTZ) produces a fusion protein whose expression gives rise to blue viral plaques in the presence of a chromogenic indicator such as 5-bromo-4-chloro-3-indolyl-β-D-galactopyranoside (X-gal).

Recombinant virus V8vEGTDEL is obtained by cotransfecting the plasmid pEGTDEL and DNA from the virus V8vEGTZ into SF cells. Homologous recombination results in the replacement of the ecrt-lacZ fusion gene in V8vEGTZ with the deleted eqt gene from pEGTDEL. The recombinant virus V8vEGTDEL is identified by its failure to form blue plaques in the presence of X-gal.

Example 16

Construction of T-NF002, an occ⁻ hβ-gal⁺ derivative of V8vEGTDEL

As a prelude to the construction of recombinant derivatives of V8vEGTDEL an intermediate virus vector is constructed in which the polyhedrin gene is partially deleted and replaced by the *Escherichia coli* lacZ gene. The resulting virus is unable to form viral occlusions (occlusion-negative; occ⁻ and gives rise to blue viral plaques in the presence of a chromogenic indicator X-gal (B-gal⁺) T-NF002 is constructed by cotransfecting SF cells with V8vEGTDEL DNA and the transfer vector pVL941-50OBgal, in which part of the AcMNPV polyhedrin gene has been replaced by the *Escherichia coli* lacZ gene (13). T-NF002 is identified as a blue plaque which is devoid of viral occlusions when the transfection supernatants are plated on SF cells in the presence of the chromogenic indicator X-gal.

Example 17

Construction of the Unloaded AcMNPV V8 Transfer Vector NF4

Transfer vector NF4 is designed to facilitate the insertion of foreign genes into the AcMNPV V8 genome by homologous DNA recombination at a site 92 bp upstream of the polyhedrin gene. To construct NF4 an 8 bp Bgl II linker (5'-CAGATCTG-3'; Boehringer-Mannheim, Indianapolis, Ind.) is first inserted into the unique Eco RV site in the polylinker of pBluescript® II KS-(Stratagene, La Jolla, Calif.), so that the Eco RV site is destroyed. This plasmid is designated AC0039.1. An Eco RI fragment extending from 0.32 m.u. to 5.83 m.u. in the AcMNPV V8 genome (Eco RI fragment "I" in FIG. 4) is then cloned into the unique Eco RI site of AC0039.1 to yield intermediate plasmid NF3.

NF4 is derived from NF3 by the net insertion of a 22 bp double stranded DNA sequence ("Bsu-Sse linker") into NF3 at a point located 92 bp upstream of the AcMNPV V8 polyhedrin gene. The inserted sequence contains recognition sites for restriction endonucleases Bsu36I and Sse83871, as shown below:

```
   Bsuu361       Sse8387I
 5'-CCTCAGGGCAGCTGCCTGCAGG-3'    (SEQ ID NO:13)

 3'-GGAGTCCCGTCGACGGACGTCC-5'    (SEQ ID NO:35)
```

Figure 6A:
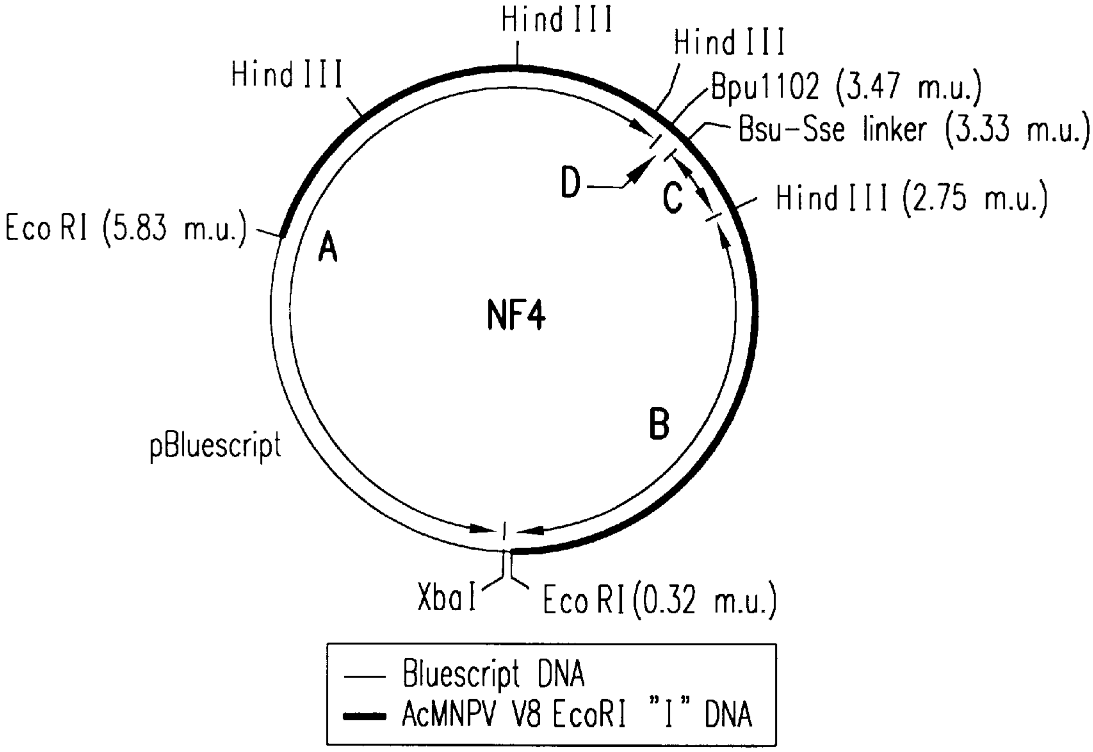
FIG. 6A depicts the manner in which fragments A–D are joined to form NF4.

Because AcMNPV V8 does not contain a convenient restriction site at the desired point of Bsu-Sse linker insertion, NF4 is assembled by simultaneous ligation of four DNA fragments, denoted A–D in FIG. 6A. All fragments are purified by agarose gel electrophoresis.

Figure 6B:
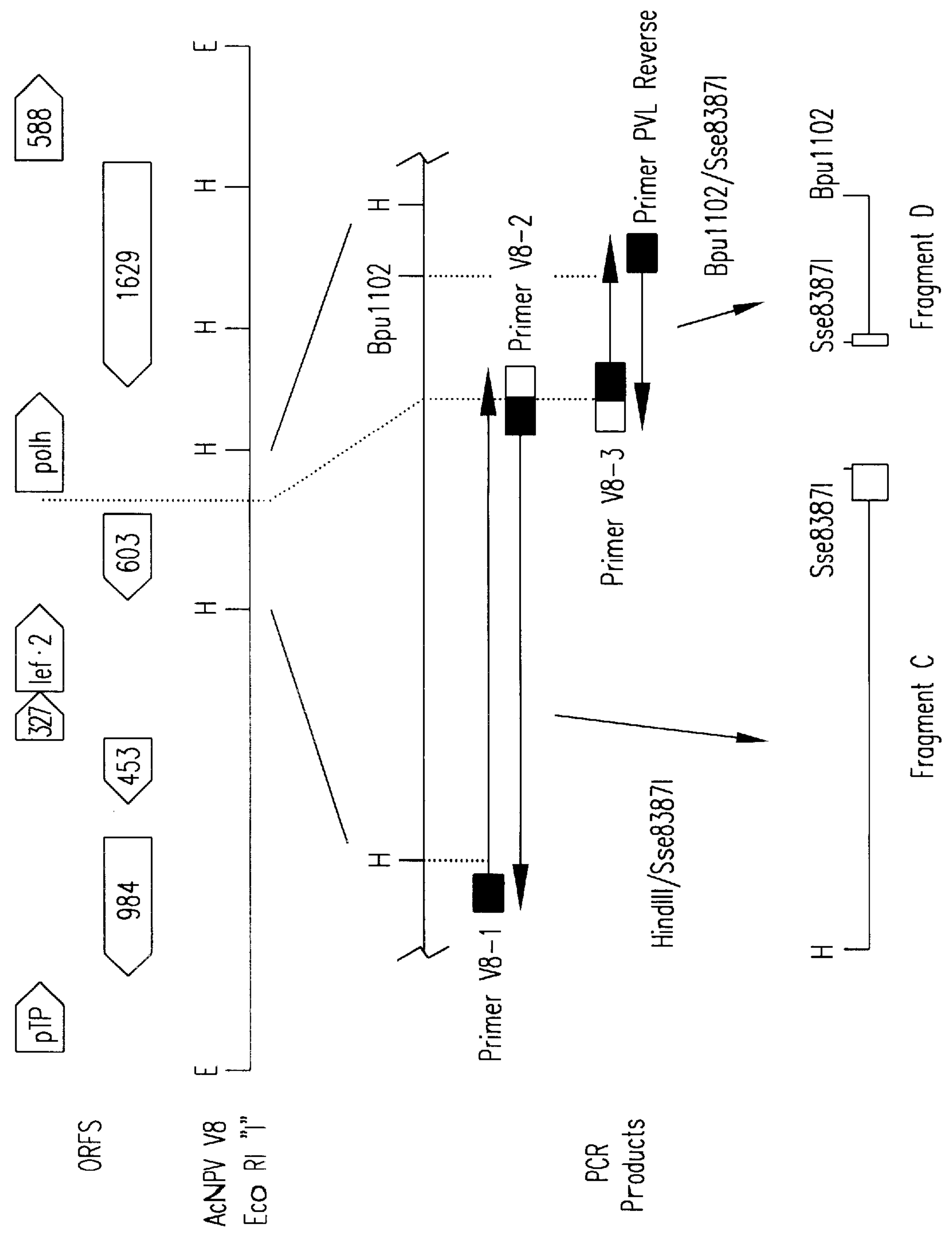
FIG. 6B depicts a schematic representation of the process used for the preparation of Fragments C and D. The arrows above the linear restriction map of the AcMNPV V8 Eco RI "I" fragment depict the location and transcriptional polarity of the major open reading frames (ORFS) located between map units 0.32 and 5.83 in the AcMNPV genome. The symbols "H" and "E" depict the positions of the recognition sites for restriction endonucleases Hind III and Eco RI, respectively.

Fragment A is prepared by digesting NF3 with restriction endonuclease Bpu1102 I, dephosphorylating the termini with calf intestine alkaline phosphatase, cleaving the DNA with Xba I and isolating the large (6.1 kb) Xba I/Bpu1102 I fragment. Fragment B is prepared by digesting NF3 with Hind III, dephosphorylating the termini with calf intestine alkaline phosphatase, cleaving the DNA with Xba I and isolating the 3.26 kb Hind III/Xba I fragment. Fragments C and D are prepared as shown in FIG. 6B from DNA fragments synthesized by PCR amplification using the AcMNPV V8 EcoRI "I" fragment in NF3 as the DNA template.

The primers for the synthesis of fragment C are:

```
V8-1:5'GCTCTGACGCATTTCTACAACCACGACTCC-3'                    (SEQ ID
                                                             NO:14)
                 Sse8387I          Bsu36I

V8-2:5'-TAATcctgcaggcagctgccctgaggATCAGCAACTATATATTAAGCCG-3'  (SEQ ID
                                                             NO:15)
```

Primer V8-1 is the forward primer in the PCR reaction and hybridizes with the complementary DNA strand of AcMNPV V8 genome at m.u. 2.65. Primer V8-2 is composed of two parts. Residues 1 through 4 and 27 through 49 (shown capitalized above) are colinear with the complementary AcMNPV V8 DNA sequence located 89 to 92 bp and 93 to 115 bp, respectively, upstream of polyhedrin gene translational start site. This segment of the primer is represented by the solid box portion of primer V8-2 in FIG. 6B. Residues 5 through 26 of primer V8-2 (shown in lower case above) comprise the complementary strand of the Bsu-Sse linker sequence being inserted 92 bp upstream of the polyhedrin gene translational start site in the AcMNPV V8 genome. This segment of the primer is not complementary to any natural AcMNPV DNA sequences and is represented by the open box portion of primer V8-2 in FIG. 6B. Following PCR synthesis, the fragment is digested with Hind III and Sse8387I to yield fragment C, which is purified by gel electrophoresis.

The primers for the synthesis of fragment D are:

Sse8387I

V8-3:5'-gctg cctcaggATTATGTAAATAATTAAAATGATAACCAT-CTCGC-3' (SEQ ID NO:16)

PVLReverse: 5'-GGATTTCCTTGAAGAGAGTGAG-3' (SEQ ID NO:17)

Primer V8-3 is composed of two parts. Residues 1 through 12 (shown in lower case above) comprise the 3' half of the top strand of the Bsu-Sse linker and are not complementary to any natural AcMNPV DNA sequences. This segment of the primer contains only the Sse8387I recognition site and is represented by the open box portion of primer V8-3 in FIG. 6B. Residues 13 through 46 are colinear with the AcMNPV V8 DNA sequence located 92 to 59 bp upstream of polyhedrin gene translational start site. This segment of the primer is represented by the solid box portion of primer V8-3 in FIG. 6B. Primer PVLReverse hybridizes to the complementary strand of the AcMNPV V8 genome at a point located 205 to 226 bp downstream of the polyhedrin gene translational start site. Following PCR synthesis, the fragment is digested with Bpu1102 I and Sse8387I to yield fragment D, which is purified by gel electrophoresis. NF4 is assembled by incubating equimolar amounts of fragments A–D (25 fmol each) for 16 h at 15° C. in a 10 μl ligation reaction containing 20 mM Tris-HCl (pH 7.5)—10 mM $MgCl^2$—10 mM DTT—0.5 mM ATP and 200 units T4 DNA ligase (New England Biolabs, Beverly, Mass.). After transformation of *E. coli* with the contents of the ligation reaction, plasmids having the structure of NF4 are identified by restriction enzyme analysis.

Example 18

Construction of a Gene Cassette Containing the *Manduca sexta* Adipokinetic Hormone Gene Signal Sequence Plus the Codon optimized cDNA Sequence Encoding AaIT Recombinant viral insecticides are viruses, especially baculoviruses, whose insecticidal properties have been enhanced by the addition of one or more foreign genes that encode insect-specific toxins (8, 24, 28), peptide hormones (25) or enzymes (32). The peptide AaIT, which is found in the venom of the North African scorpion *Androctonus australis*, is an example of such an insect-specific toxin (28). When AaIT is injected into the body cavity of an insect larva, it binds selectively to voltage-sensitive sodium channels and causes a contractile paralysis. Chronic administration of the toxin, which can be achieved by infecting insect larvae with AaIT producing viruses, is associated with a prolonged state of paralysis and eventual death.

A gene cassette encoding the mature AaIT toxin linked to an insect signal peptide from the *Manduca sexta* adipokinetic hormone (ADK) gene is synthesized and assembled in two pieces: A "B" fragment consisting of DNA coding for the ADK signal sequence plus the amino terminal portion of the toxin coding region, and an "A" fragment, which encodes the remainder of the toxin coding region. Each of fragments A and B is made by annealing a pair of oligomers containing a 15 bp overlap purchased from New England Biolabs (Beverly, Mass.). Sequenase™ 2.0, a DNA polymerase (United States Biochemical Corporation, Cleveland, Ohio), is used to complete the double stranded molecule, which contains the ADK signal sequence plus the codon optimized cDNA sequence encoding AaIT. The following is a list of the oligomers used in the construction of this construct:

Fragment A

```
E1   5'AGCCCCCGAG TGCCTGCTCT CGAACTATTG
```

-continued

```
          CAACAATGAA TGCACCAAGG TGCACTACGC
          TGACAAGGGC TACTGTTGCC TTCTGTCCTG
          CTATTGCTTC 3'(SEQ ID NO:18)
E2      5'CTGTAGGTAC CGGATCCTTA GTTAATGATG
          GTGGTGTCAC AGTAGCTCTT GCGAGTATCA
          GAGATTTCCA GAACTTTCTT GTCGTCGTTG
          AGACCGAAGC AATAGCAGGA 3'(SEQ ID NO:19)
```

Fragment B2

```
Common  5'AGGCACTCGG GGGCTTTTCC GGATGAGGTC
          GACTGCGTAG CCGTTCTTCT T 3'(SEQ ID NO:20)
ADK     5'CCCCCCGGAT CCATGTACAA ACTGACCGTC
          TTCCTGATGT TCATCGCCTT CGTGATTATC
          GCTGAGGCCA AGAAGAACGG CTAC3'
          (SEQ ID NO:21)
```

FIG. 7 depicts the construction strategy for the gene cassette which contains the AaIT gene linked to the *Manduca sexta* ADK signal sequence. In the first step, oligonucleotides 'Common' and 'ADK' are annealed and the single stranded regions are filled in using Sequenase™ 2.0. The filled in fragment consists of a 12 nuclectide upstream noncoding region containing the BamHI site required for cloning, the coding region for the ADK signal sequence, and the first 15 nucleotides encoding the first five aminoterminal amino acids of AaIT. This short piece of double-stranded DNA is digested with Bam HI and Ava I and subcloned into pBluescript SK+(Stratagene, LaJolla, Calif.) which has been digested with Xma I and Bam HI. Positive subclones are verified by the presence of a Pvu II fragment larger than the 445 bp fragment present in pBluescript SK+ alone. There is a single base pair mismatch between the overhangs for the Ava I and Xma I sites. Clones which have corrected this mismatch are selected by the appropriate restriction enzyme digestions. In FIG. 7, the resulting plasmid is designated pBS ADK B2.

To construct the A fragment encoding the bulk of the AaIT coding region, oligonucleotides 'E1' and 'E2' are annealed and Sequenase-' 2.0 is used to fill in the single stranded regions. This results in a double-stranded molecule which contains an Ava I site at the 5' terminus and nested Bam HI and Asp 718 sites following the 3' end of the toxin coding region. The Bam HI and Asp 718 sites are introduced in order to facilitate cloning. Fragment A is then digested with Ava I and Asp 718. The fragment B2-containing plasmid, pBS ADK B2, is also digested with Ava I and Asp 718 and Fragment A is subcloned into the digested plasmid. In FIG. 7, the resulting plasmid is designated pBS ADK-AaIT. After the ligation of fragment A into pBS ADK B2, the ligated DNA is used to transform competent DH5 *E. coli*. Minipreps of plasmid DNA are prepared from the resulting bacterial colonies. Restriction enzyme analysis is used to determine which colonies contain the desired recombinant DNA. Further restriction enzyme analysis, followed by DNA sequencing, is used to confirm the integrity of plasmid pBS ADK-B2.

Example 19

Insertion of the ADK-AaIT Gene Cassette into occ⁻ Baculovirus Transfer Vectors

The ADK-AaIT gene cassette of Example 18 is isolated as a Bam HI fragment from pBS ADK-AaIT and subcloned into the pVL985 baculovirus transfer vector DNA (13) which had been digested with Bam HI and treated with calf intestine alkaline phosphatase. The resulting plasmid is designated pVL985/A-DK-AaIT. Restriction enzyme analysis followed by sequencing of the insert is used to confirm the correct orientation and integrity of pVL98S/ADK-AaIT.

Samples of an *E. coli* strain HB101 harboring the transfer vector AC0055.1 have been deposited previously by applicants' assignee with the American Type Culture Collection, 12301 Parklawn Drive, Rockville, Md. 20852, U.S.A. and have been assigned ATCC accession number 69166. AC0055.1 contains a gene cassette in which the AaIT gene sequence of Example 48 is linked to a Drosophila cuticle gene signal sequence rather than the *Manduca sexta* adipokinetic hormone gene signal sequence. Using this deposited material, one of ordinary skill in the art can substitute the adipokinetichormnone gene signal sequence described above for the cuticle gene signal sequence which has the following DNA sequence:

Cuticle 5'CCCCCCGGAT CCATGTTCAA GTTCGTGATG ATCTGCGCCG TCCTCGGCCT GGCTGTGGCC AAGAAGAACG GCTAC 3' (SEQ ID NO:22)

Example 20

Insertion of the ADK-AaIT Gene Cassette into Baculovirus Modular Expression Vectors Since the ADK-AaIT gene cassette in the pVL985/ADK-AaIT transfer vector of Example 19 replaces part of the viral polyhedrin gene, the usefulness of this transfer vector is limited to the construction of occlusion-negative (occ⁻) recombinant viruses that express AaIT. It is also advantageous to insert the ADK-AaIT into the AcMNPV genome at a site which allows the recombinant virus to form viral occlusion bodies. One site which is useful for this purpose is the site of Bsu-Sse linker in the (unloaded) AcMNPV V8 transfer vector NF4 of Example 17. This site is located between the viral polyhedrin and ORF 603 open reading frames and does not disrupt any known viral functions (cf FIG. 6). However, since the ADK-AaIT gene cassette of Example 18 does not contain the regulatory sequences necessary for the transcription and 3' processing (polyadenylation) of ADK-AaIT mRNA, it is first necessary to insert the ADK-AaIT gene cassette into an expression vector which supplies these critical regulatory elements. One such vector is pMEV1.1, which is an Esp 3'-based Modular Expression Vector based on the general design shown in FIG. 8. pMEV1.1 is constructed in pBluescript KS- and is comprised of the following components: (1) a virus insertion module, which is delineated by recognition sites for restriction enzymes Sse 8387I and Bsu 36I; (2) a promoter module, which in the case of pMEV1.1 consists of the promoter and 5' untranslated region of the AcMNPV DA26 gene (17); (3) a polylinker module, which is used to facilitate insertion of the gene cassette whose expression is desired; and (4) a 3' UTR (untranslated region) which supplies a site for the 3' processing and polyadenylation of mRNA. The 3' UTR in pMEV1.1 consists of the 3' UTR of the AcMNPV basic protein (6.9K) gene (15). Samples of an *E. coli* strain DH5 harboring pMEV1.1 (AC0064.1) have been deposited by applicants' assignee with the American Type Culture Collection, 12301 Parklawn Drive, Rockville, Md. 20852, U.S.A., on Apr. 7, 1993, and have been assigned ATCC accession number 69275.

Figure 9:
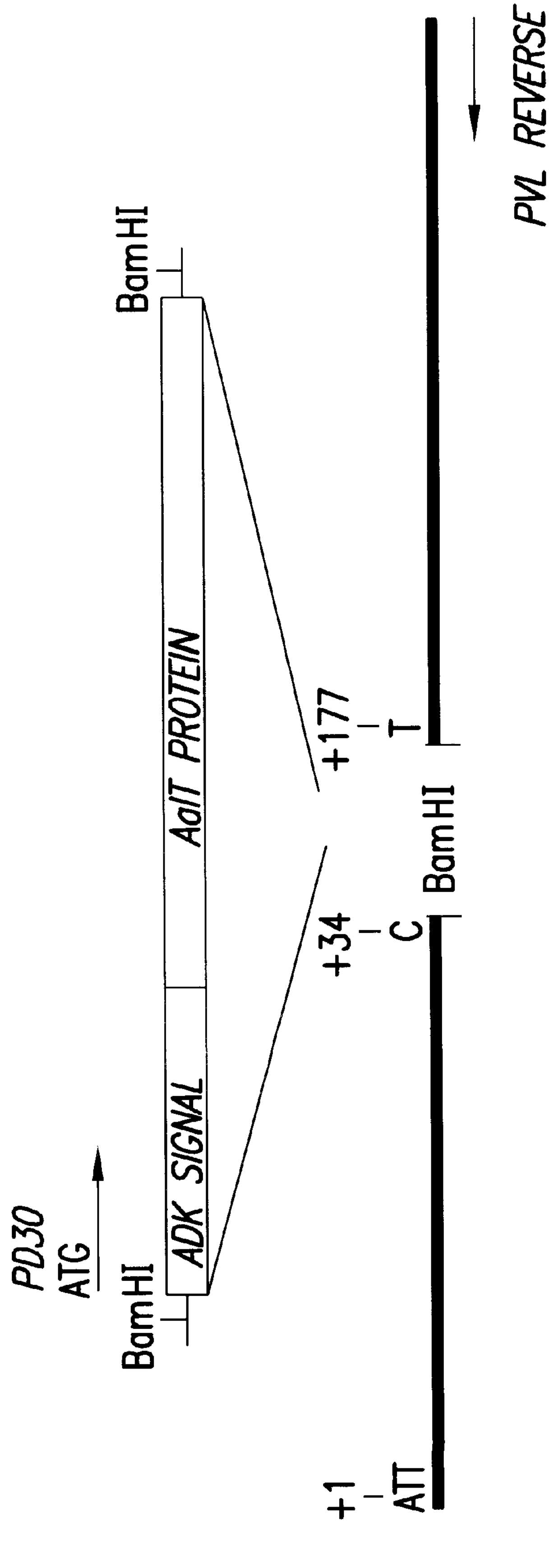

To insert the ADK-AaIT gene cassette into pMEV1.1, the ADK-AaIT gene cassette is first recovered from the pVL985/ADK-AaIT transfer vector of Example 18 by PCR. The PCR strategy is shown in FIG. 9. The (+)strand primer used for this reaction is oligonucleotide PD30, whose 5' terminus coin~ides with the ATG translation initiation codon of the ADK-AaIT gene. The sequence of PD30 is as follows:

PD30 5'-ATGTACAAACTGACCGTCTTCCTGATG-3' (SEQ ID NO:23)

The (−)strand primer in each case is PVLReverse (SEQ ID NO:5) (see Example 17), which hybridizes to a site located 20S to 226 bp downstream of the polyhedrin gene translational start site, or about 35 bases downstream of the site of ADK-AaIT gene insertion in the pVL985/ADK-AaIT template.

For the amplification reaction, 50 pmol of each primer is combined with 250 pg of pVL985/ADK-AaIT template DNA in a 50 μl reaction mixture containing 10 mM Tris-HCl (pH 8.3), 50 mM KCl, 1.5 mM $MgCl^2$, 200 μM dNTPs, 100 μg/ml gelatin and 2.5 units AmpliTaq™ DNA polymerase (Perkin-Elmer Cetus, Norwalk, Conn.). The reaction is the incubated through 25 cycles of 1 minute at 94° C. (denaturation step), 1.5 minutes at 55° C. (annealing step), and 3.0 minutes at 72° C. (extension step). This is followed by a single 7 minute extension at 72° C. The reaction is then terminated by the addition of EDTA to 10 mM and Sarkosyl (sodium N-lauroylsarcosine) to 0.2% (w/v).

The product is extracted once with phenol:chloroform and precipitated with ethanol. After collection the product is treated with the Klenow fragment of *E. coli* DNA polymerase I in the presence of all four dNTPs to ensure that the PCR product has a blunt 5' terminus. The 3' terminus of the ADK-AaIT toxin gene cassette is then defined by digesting the product with Bam HI, and the ADK-AaIT containing fragment is purified by electrophoresis on a 1.8% agarose gel.

To prepare the pMEV1.1 for toxin gene insertion, the DNA is digested with Esp 3I and the resulting 5' protruding termini are filled in by the action of *E. coli* DNA polymerase I (Klenow fragment) in the presence of all four dNTPs. The DNA is then digested with Bam HI and the vector is separated from the liberated polylinker fragment by electrophoresis on a 1% low melt agarose gel. The blunt/Bam HI vector fragment is then ligated with an equimolar amount of the blunt/Bam HI ADK-AaIT fragment and transfected into *E. coli*. The resulting plasmid is designated pMEV1.1/ADK-AaIT-1 (AC0075.1) and contains the ADK-AaIT coding region under the control of the AcMNPV DA26 gene promoter. A schematic representation of the virus insertion module in pMEV1.1/ADK-AaIT-1 (AC007S.1) is presented in FIG. 10.

Example 21

Construction of Recombinant Virus V8vEGTDEL-AaIT

To construct a recombinant derivative of V8vEGTDEL containing the ADK-AaIT gene under the control of the AcMNPV DA26 promoter plasmid pMEV1.1/ADK-AaIT-1 is digested with restriction enzymes Bsu 36I and Sse 83871, and the virus insertion module containing the DA26/ADK-AaIT expression cassette is purified by agarose gel electrophoresis. This fragment is inserted into the Bsu-Sse linker of transfer vector NF4 of Example 17. The resulting transfer vector is designated NF5 and contains the DA26/ADK-AaIT expression cassette positioned 92 bp upstream of the translational start site of the polyhedrin gene, such that the transcriptional polarity of the AaIT gene is opposite that of the polyhedrin gene.

Construction of a recombinant virus containing the AaIT gene is accomplished by co-transfecting Sf9 cells with T-NF002 viral DNA and transfer vector NF5, using procedures described by Summers and Smith (6). Since the T-NF002 virus of Example 16 contains the *E. coli* lacZ gene in place of the viral polyhedrin gene, recombinant between T-NF002 and the transfer vector NF5 are identified as colorless occlusion-positive plaques when the virus is grown on Sf9 cells in the presence of the chromogenic substrate X-gal. This virus is designated V8vEGTDEL-AaIT and contains the DA26/ADK-AaIT expression cassette positioned 92 bp upstream of a fully functional polyhedrin gene.

Example 22

Preparation of V8vEGTDEL-AaIT Occlusion Bodies

Occlusion bodies (polyhedra) from V8vEGTDEL AaIT are formed by infecting Sf9 cells in culture and harvesting the occlusion bodies 5 days post-infection. Briefly, Sf9 cells are maintained at 27° C. in logarithmic growth in spinner cultures at densities of $0.3\times10^6$to $4.0\times10^6$ cells per ml in complete TNM-FH medium (prepared as described by Summers and Smith (6)). For occlusion body production the cultures are infected at a density of $1.0\times10^6$ cells/ml with V8vEGTDEL-AaIT budded virus at a multiplicity of infection of 0.1–1.0 plaque forming units per cell. After 5 days of incubation at 27° C., intact cells, cell debris and occlusion bodies are collected at 2000 rpm for 10 minutes in a Beckman GPR centrifuge at 4° C. The pellet is resuspended at an equivalent of $10\ ^7$cells/ml in 50 mM Tris-HCl (pH 7.5)—10 mM EDTA—0.1%. (v/v) Triton X-100. Sodium dodecyl sulfate (SDS) is added to a final concentration of 1% (w/v) and the liberated cellular DNA is sheared by vigorous pipeting. The occlusion bodies are collected by centrifugation at 2000 rpm for 10 minutes, washed twice by centrifugation with 50 mM Tris-HCl (pH 7.5)—10 mM EDTA—0.1%—. Triton X-100 and then resuspended at a density of approximately $10^9$ occlusion bodies per ml in sterile distilled water. The yield is typically in the range of $2\times10^{10}$ occlusion bodies per liter of original culture.

REFERENCES

1. Smith, G. E., and Summers, M. D., U.S. Pat. No. 4,745,051.
2. Francki, R. I. B., et al., eds., “Classification and Nomenclature of Viruses” in *Archives of Virology*, Supp. 2, pages 117–123 (1991).
3. Luckow, V. A., and Summers, M. D., *Bio/Technoloy* 6, 47–53 (1988).
4. Webb, N. R., and Summers, M. D. *Technique*, 2, 173–188 (1990).
5. Kitts, P. A. et al., *Nucl. Acids Res.*, 18, 5667–5672 (1990
6. Summers, M. D., and Smith, G. E., *A Manual Of Methods For Baculovirus Vectors and Insect Cell Culture Procedures*, Dept. of Entomology, Texas Agricultural Experiment Station and Texas A & M University, College Station, Texas 77843–2475, Texas Agricultural Experiment Station Bulletin No. 1555 (1987).
7. Granados, R. R., and Federici, B. A., *The Biology of Baculoviruses*, 1, 99 (1986).
8. Tomalski, M. D., and Miller, L. K., *Nature*, 352, 82–85 (1991).
9. Zlotkin, E., et al., *Toxicon*, 9, 1–8 (1971)
10. Sambrook, J., et al., *Molecular Cloning: A Laboratory Manual*, $2^{nd}$ ed., Cold Spring Harbor Laboratory Press, Cold Spring Harbor, N.Y. (1989)
11. Emery, and Bishop, *Protein Engineering*, 1, 359–366 (1987).
12. Wang, et al., *Gene*, 100, 131–137 (1991).
13. Luckow, V. A., and Summers, M. D., *Virology*, 170, 31–39 (1989).
14. Malitschek, B., and Schartl, M., *BioTechniques*, 11, 177–178 (1991)
15. Wilson, M. E., et al., *J. Virology*, 61, 661–666 (1991).
16. Hill-Perkins, M. S., and Possee, R. D., *J. Gen Virology*, 71, 971–976 (1990).
17. O'Reilly, D. R., et al., *J. Gen. Virology*, 71, 1029–1037 (1990)
18. Friesen, P. D., and Miller, L. K., *J. Gen. Virology*, 71 2264–2272 (1987)
19. Morris, and Miller, *J. Virology*, 66, 7397–7405 (1992)
20. Cochran, M., and Faulkner, P., *J. Virology* 45, 961–970 (1983)
21. Guarino, L. and Dong, W., *J. Virology*, 65, 3676–3680 (1991).
22. Guarino, L. A., et al., *J. Virology*, 60, 215–223 (1986).
23. Pearson, M. R., et al., *Science*, 257 1382–1384 (1992).
24. Stewart, L. M. D., et al., *Nature*, 352, 85–88 (1991).
25. Maeda, S., *Biochem. Biophys, Res. Commun.*, 165, 1177–1183 (1989).
26. Bougis, P. E., et al., *J. Biol. Chem.*, 264, 19259–19265 (1989).
27. Grace, T. D. C., *Nature*195, 788–789 (1962).
28. Jackson, J. R. H., and Parks, T. N., U.S. Pat. No. 4,925,664.
29. Martens, J. W. M., et al., *App. & Envir. Microbiology*, 56, 2764–2770 (1990).
30. Federici, B. A., *In Vitro*, 28, 50A (1992).
31. Casadaban, M. J., et al., *Methods Enzymol.*, 100, 293–303 (1983)
32. Hammock, B. D., et al., *Nature*, 344, 458–461 (1990)
33. Some Examples are provided in N. Webb et al., U.S. Application and the corresponding PCT application, and in copending U.S. application Ser. No. 08/322,679 filed Oct. 13, 1995, each of which is incorporated herein by reference.

We claim:

1. A recombinant insect virus comprising a heterologous gene which is operably linked to an early promoter, wherein the insect virus is a nuclear polyhedrosis virus; the heterologous gene encodes an insect controlling or modifying substance selected from the group consisting of LqhIT2, LqqIT2, BjIT2, LqhP35, SmpIT2, SmpCT2, SmpCT3, SmpMT, DK9.2, DK11, KD12, $\mu$-agatoxins, King Kong toxin, Pt6, NPS-326, NPS-331, NPS-373, and Tx4(6-1); and the early promoter is selected from the group consisting of 35K and DA26.

2. The recombinant insect virus of claim 1 wherein the insect virus is a baculovirus.

3. A method of expressing an insect controlling or insect modifying substance in insect cells comprising infecting insect cells with a recombinant virus of claim 1.

4. An insecticidal composition comprising the recombinant insect virus of claim 1.

5. A method of protecting plants from damage from insects which comprises delivering to said plant an recombinant insect virus of claim 1.

6. The recombinant insect virus of claim 1 selected from the group consisting of *Autographa californica* MNPV and *Helicoverpa zea* NPV.

7. The recombinant insect virus of claim 1, wherein the promoter is a 35K promoter.

8. The recombinant virus of claim 1, wherein the promoter is a DA26 promoter.

9. A recombinant insect virus comprising a heterologous gene which is operably linked to an early promoter and encodes an insect controlling or modifying substance, wherein the insect virus is a nuclear polyhedrosis virus; the insect controlling or modifying substance is AaIT; and the early promoter is 35K.

10. The recombinant insect virus of claim 9 wherein the insect virus is a baculovirus.

11. A method of expressing an insect controlling or insect modifying substance in insect cells comprising infecting insect cells with a recombinant baculovirus of claim 9.

12. An insecticidal composition comprising the recombinant insect virus of claim 9.

13. A method of protecting plants from damage from insects which comprises delivering to said plant an recombinant insect virus of claim 9.

14. The recombinant insect virus of claim 9 selected from the group consisting of *Autographa californica* MNPV and *Helicoverpa zea* NPV.

* * * * *